(12) United States Patent
Martin et al.

(10) Patent No.: US 7,177,390 B2
(45) Date of Patent: Feb. 13, 2007

(54) DIGITAL X-RAY TOMOSYNTHESIS SYSTEM

(75) Inventors: Peter Martin, Haiku, HI (US); Brett Spivey, Carlsbad, CA (US)

(73) Assignee: Trex Enterprises Corp, San Diego, CA (US)

( * ) Notice: Subject to any disclaimer, the term of this patent is extended or adjusted under 35 U.S.C. 154(b) by 0 days.

(21) Appl. No.: 11/077,666

(22) Filed: Mar. 10, 2005

(65) Prior Publication Data

US 2005/0226369 A1 Oct. 13, 2005

Related U.S. Application Data

(60) Provisional application No. 60/646,014, filed on Jan. 22, 2005, provisional application No. 60/552,429, filed on Mar. 11, 2004.

(51) Int. Cl.
*G01N 23/00* (2006.01)
(52) U.S. Cl. .......................................... 378/25; 378/21
(58) Field of Classification Search .................. 378/21, 378/22, 23, 25, 901, 26
See application file for complete search history.

(56) References Cited

U.S. PATENT DOCUMENTS

| | | | |
|---|---|---|---|
| 6,201,850 B1 * | 3/2001 | Heumann | 378/56 |
| 2005/0135664 A1 * | 6/2005 | Kaufhold et al. | 382/131 |

* cited by examiner

Primary Examiner—Edward J. Glick
Assistant Examiner—Hoon Song
(74) Attorney, Agent, or Firm—John R. Ross

(57) ABSTRACT

Method and device for digital x-ray tomosynthesis. Tomographic and/or three-dimensional images of an object are obtained with an x-ray source and a digital x-ray image sensor. The source, object and sensor are positioned relative to each other and attenuation data is obtained for a large number of rays of x-radiation through the object. A special algorithm is provided to convert the data into images. To calculate the images the algorithm uses iterative processes with a least squares type technique but with generalized (as opposed to specific) functions. The algorithm solves for the functions which are the images. Preferred embodiments include a system having an x-ray point source with a cone of diverging x-rays, a two-dimensional digital x-ray image sensor, two linear translation stages to independently move both the x-ray source and the digital x-ray image sensor, two rotation mechanisms to rotate the two linear translation stages, a microprocessor to control the data acquisition, and a computer programmed with a special algorithm to calculate the tomographic images. A plurality of sets of digital data (representing x-ray algorithm images of an object) are acquired by the digital x-ray image sensor, with the x-ray source and the digital x-ray image sensor located at different positions and angles relative to the object. The digital data representing the x-ray attenuation images is stored in the computer. Special mathematical algorithms then compute multiple images of the object using the acquired digital data. These images could include multiple tomographic images, a three-dimensional image, or a multiple three-dimensional images.

19 Claims, 17 Drawing Sheets

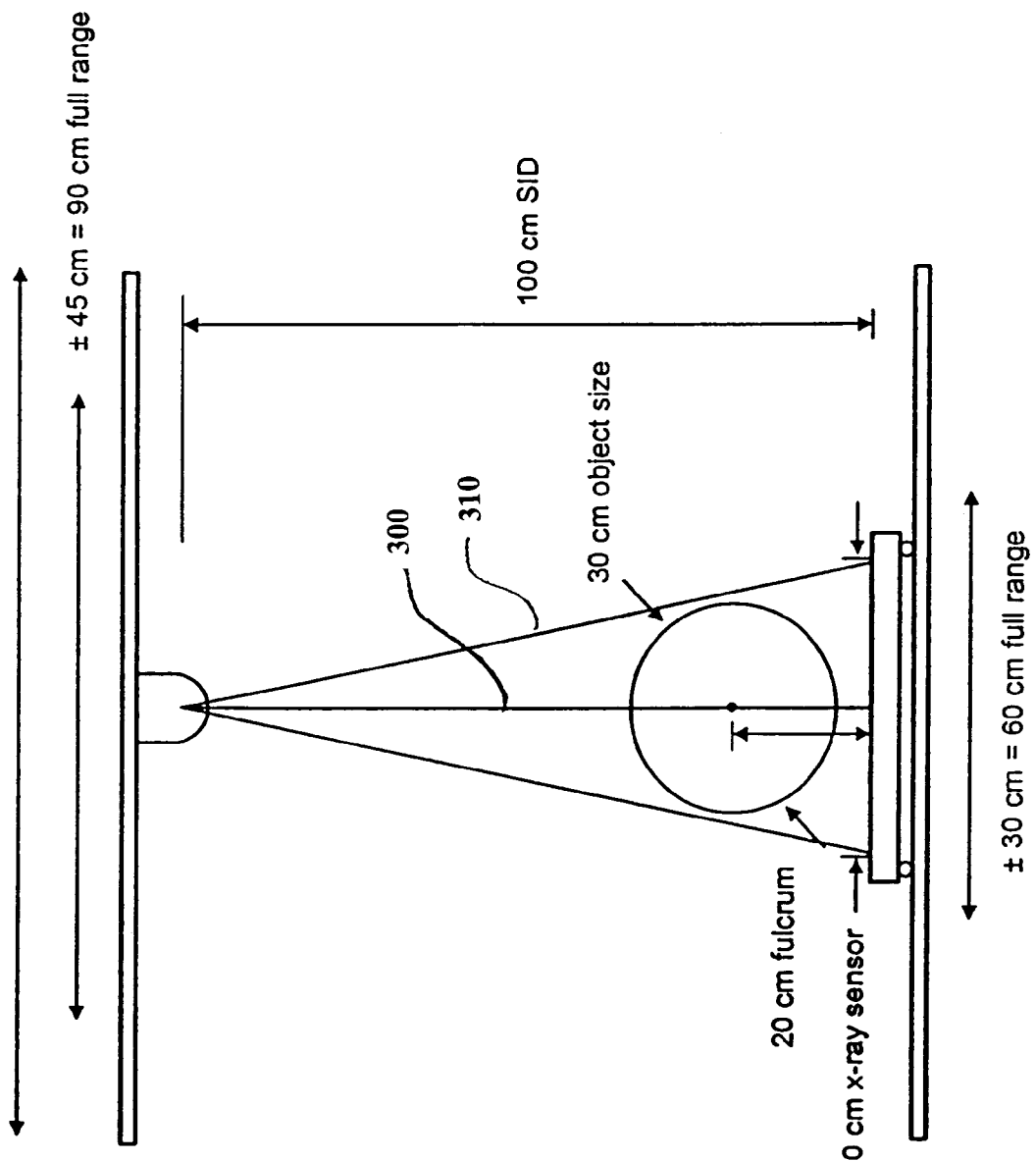
FIG. 6A(1)

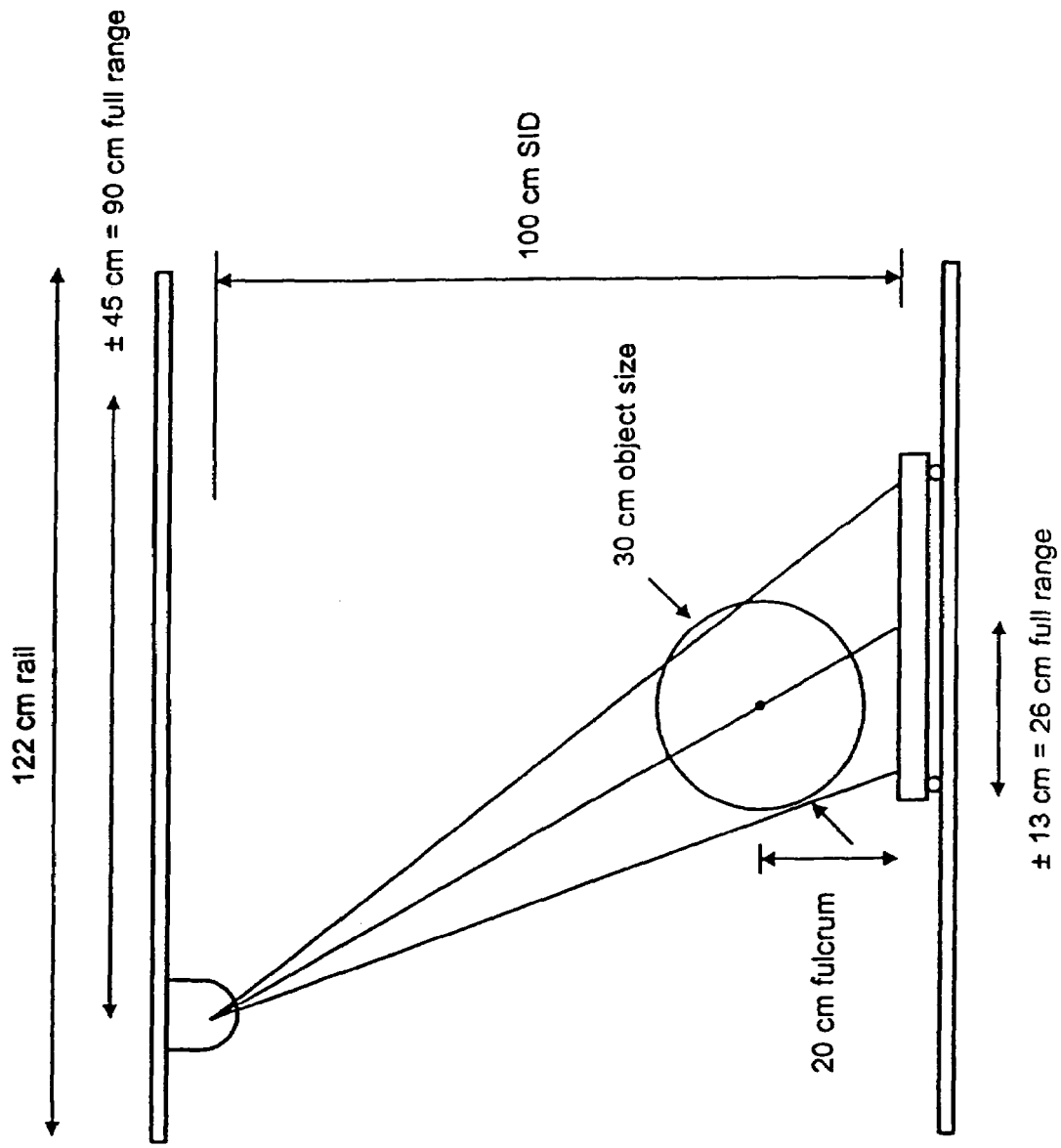
FIG. 6A(2)

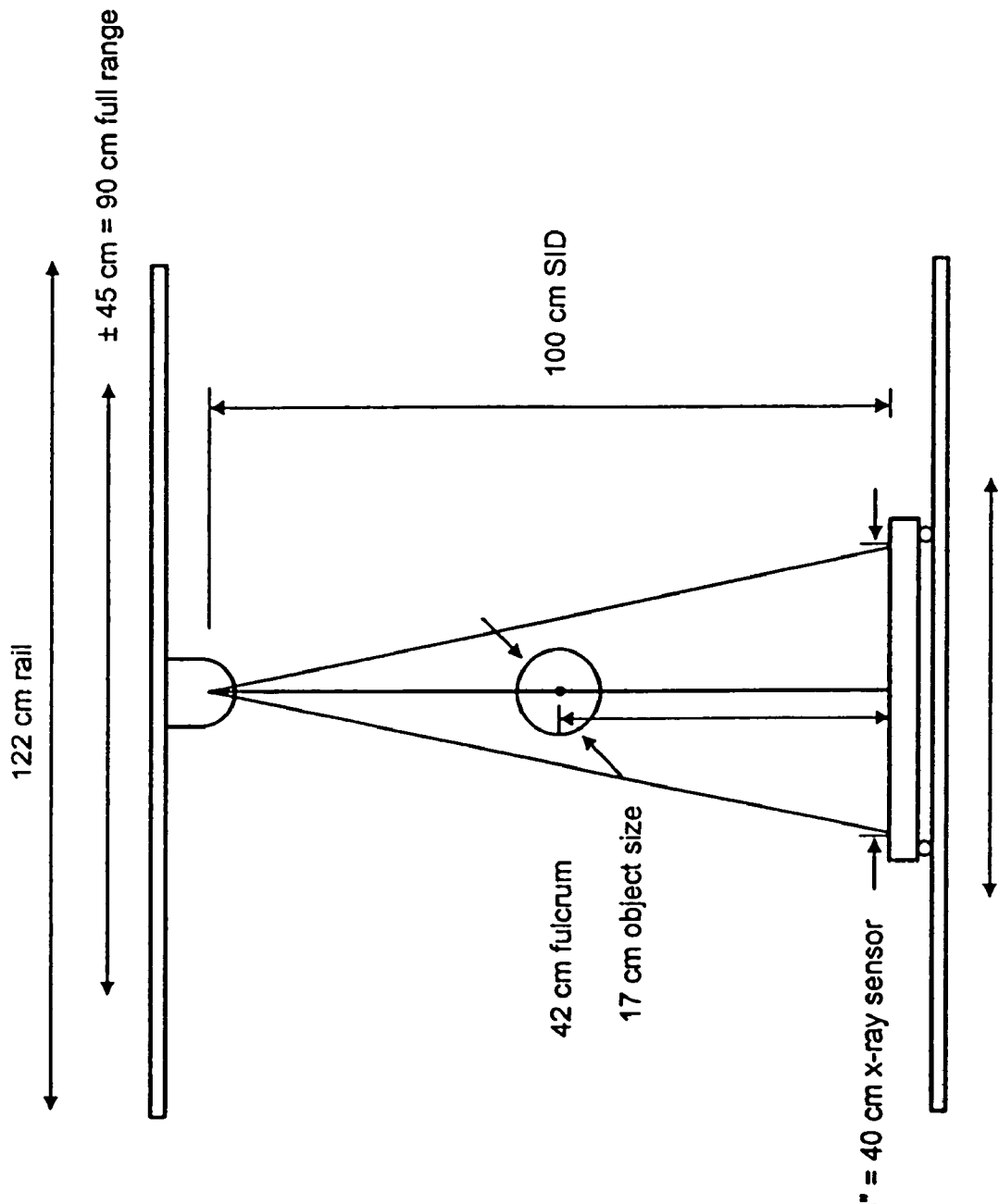
FIG. 6B(1)

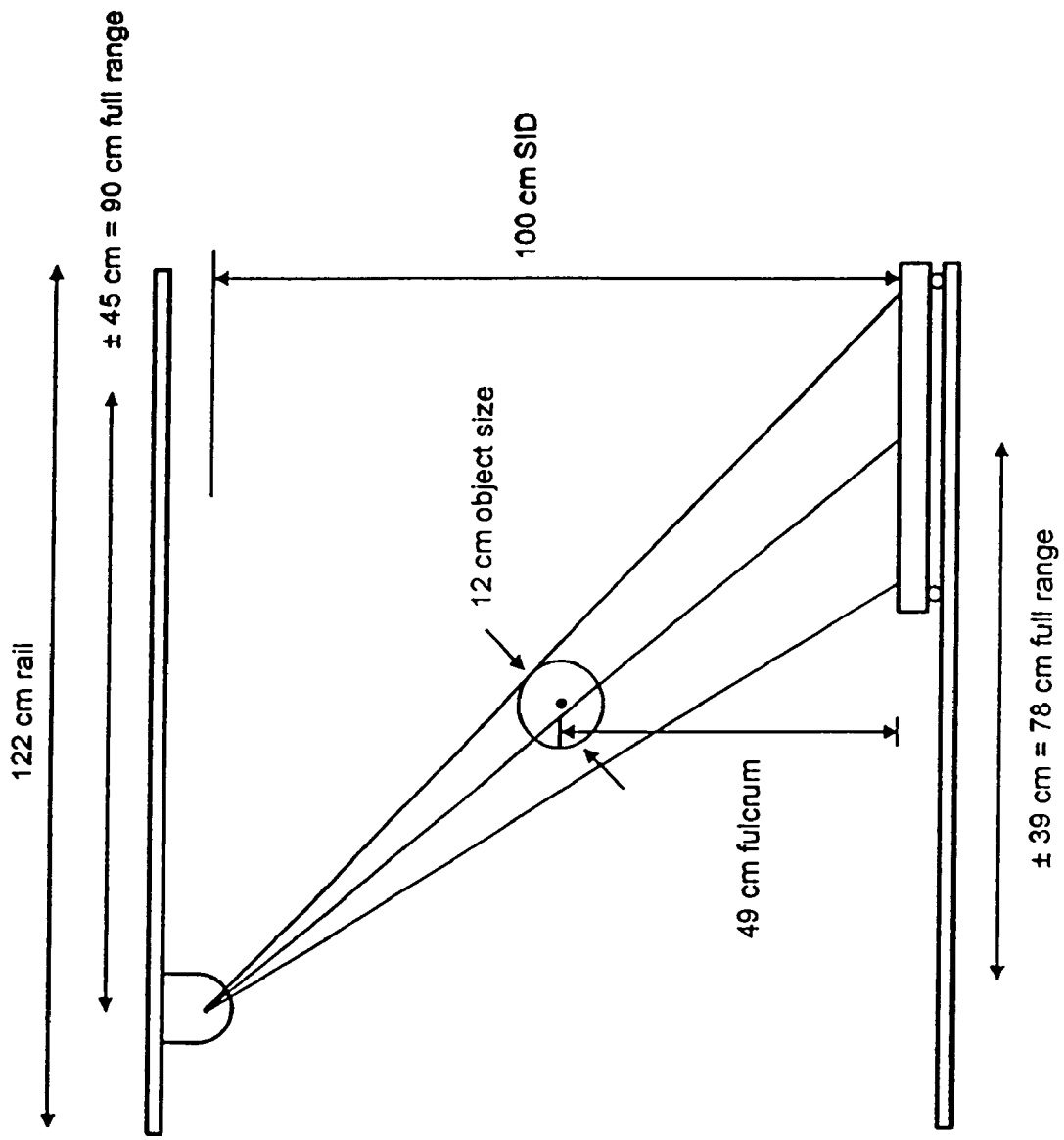
FIG. 6B(2)

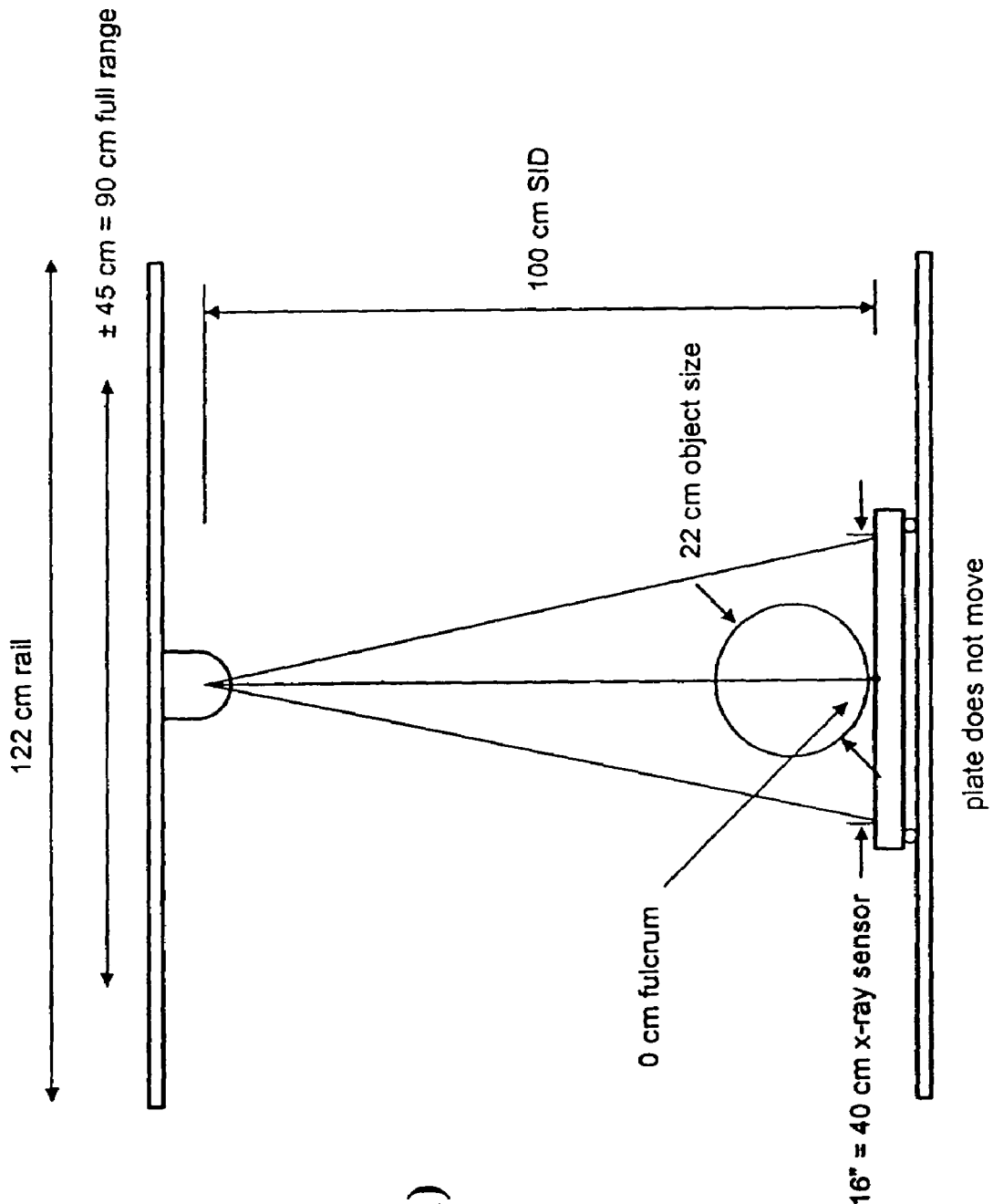
FIG. 6C(1)

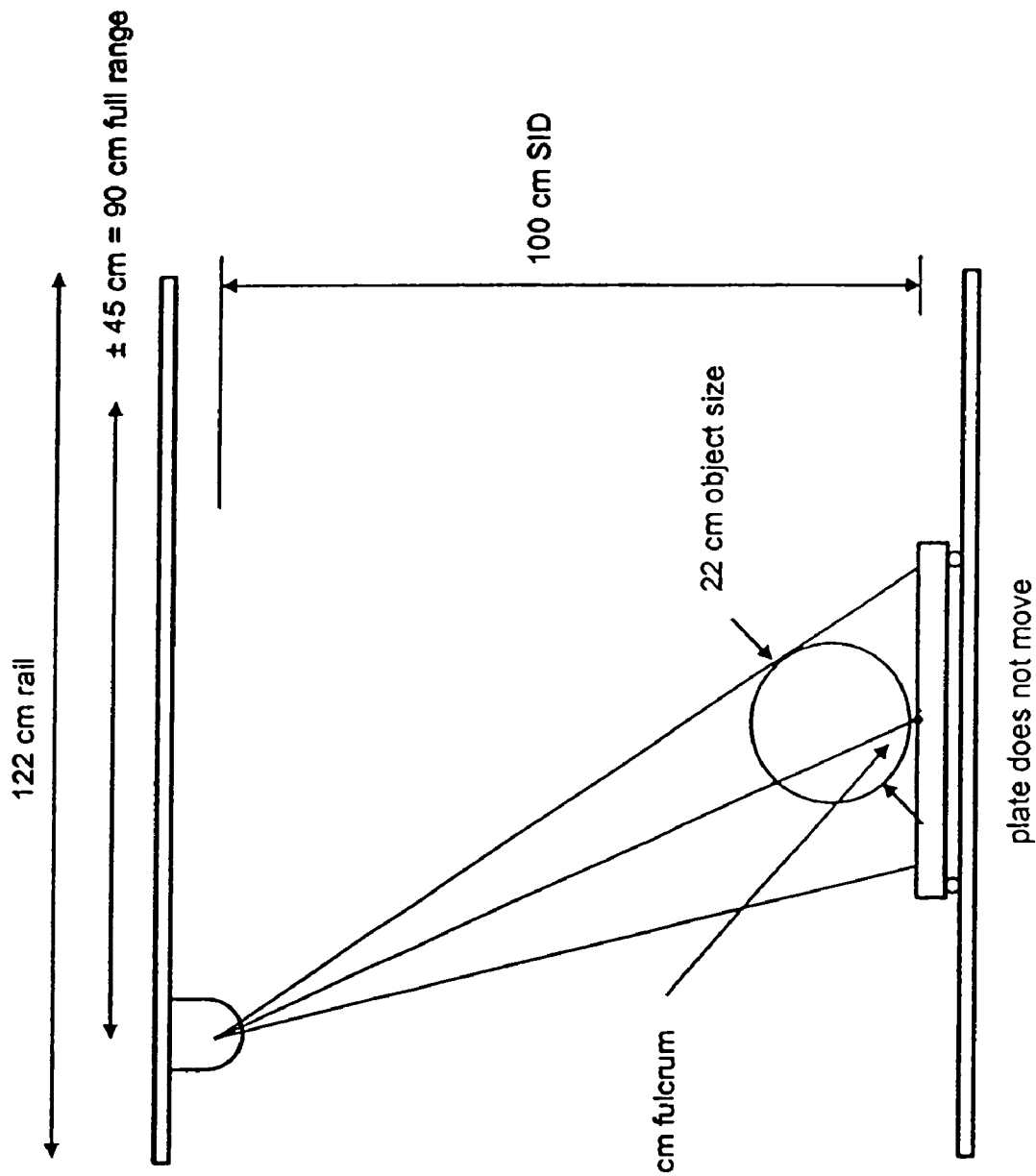
FIG. 6C(2)

DIGITAL X-RAY TOMOSYNTHESIS SYSTEM

This application claims the benefit of provisional patent application Ser. No. 60/552,429 filed Mar. 11, 2004 and provisional patent application Ser. No. 60/646,014 filed Jan. 22, 2005. This invention relates to digital x-ray systems, and in particular, digital x-ray tomosynthesis systems.

BACKGROUND OF THE INVENTION

The prior art x-ray imaging systems include projection radiography, geometric tomography, projection radiography, computed axial tomography, and digital x-ray tomosynthesis methods, as described here. These x-ray systems have many applications, especially medical imaging and security applications such as baggage imaging. Projection radiography is a imaging technique involving an x-ray point source that emits a cone beam of x-rays through an object, and a two-dimensional x-ray image sensor (i.e. x-ray film or digital x-ray image sensor, for example) that measures the spatially varying attenuation of the x-ray cone beam after is passes through the object.

Geometric Tomography

Geometric tomography (GT), invented in the 1930s, involves a method for using a conventional film-based x-ray imaging system to provide radiographic images in tomographic slices. This method, displayed in FIG. 1, incorporates the co-motion of x-ray source 10 and image receptor 40 (i.e. x-ray film, for example) during the x-ray exposure. The co-motion of x-ray source 10 and film 40, relative to imaged object 25, produces an image on x-ray film 40 with a sharp focus at image plane 35 containing the fulcrums of motion 30, 31 and 32. The spatially varying x-ray attenuation above and below image plane 35 is essentially "blurred" out by the relative co-motion. Different image planes 35 can be imaged on different sheets of film 40, by varying the different velocities of x-ray source 10 and film 40 relative to imaged object 25. The GT imaging method showed potential for improved diagnostic efficacy compared to conventional projection radiography, however, this method required much higher x-ray doses, mainly because each GT image required an equivalent x-ray dose as a projection radiograph. The dose issue resulted in limited clinical deployment of the GT method.

Computed Axial Tomography

During the 1970s, the development of computed axial tomography (CAT) methods provided a revolution in diagnostic radiography and a widespread clinical deployment of the CAT systems. The process is referred to as a "CAT scan." A typical CAT system features an x-ray point source and spatial filtration (i.e. a slit) so that the x-ray source emits a fan beam of x-rays. A linear (i.e. one-dimensional) pixelated array of high performance x-ray detectors measures the attenuation of the x-ray fan beam after it passes through an object, such as a human body, for example. This system rotates 360 degrees around an object and provides x-ray attenuation data in a plurality of planes (planes of rotation) at a plurality of regularly spaced angles. The computer calculates a digital tomographic image of the object for each of the planes of the rotation. To do this the system moves to a plurality of positions perpendicular to the planes of rotation and repeats the imaging procedure to provide the plurality of tomographic images of the object. These tomographic images can be viewed separately, or can be processed by the computer to provide three-dimensional images of the object. With the CAT scan technique, all data is obtained with the x-ray source and the detectors in fixed positions relative to the object being imaged so there is no intentional blurring of any of the image information.

Digital X-ray Tomosynthesis

In the 1960–1970s, the development of fluoroscopic cameras, comprised of image intensifier tubes coupled to video sensors, enabled the emergence of digital x-ray tomosynthesis methods. A digital projection radiograph involves an x-ray point source that emits a cone beam of x-rays, and a digital x-ray image sensor comprised of a two-dimensional array of x-ray detectors (fluoroscopic camera, for example) that measures the spatially varying attenuation of the x-ray cone beam after is passes through an object. Digital x-ray tomosynthesis (DXT) involves the acquisition of a plurality of digital projection radiographs of an object with the x-ray source and the x-ray image sensor located at different positions and angles relative to the object. A computer then uses the digital data to compute a plurality of tomographic images of the object.

The DXT method, in the simplest sense, provides x-ray attenuation data and calculations that emulate the motional blurring of the GT method to visualize the single image plane at the fulcrum of motion of the x-ray source and image sensor. However, the DXT method provides a much more dose efficient radiographic modality than the earlier GT method because the DXT method enables the computation of a plurality of tomographic images from a single set of multi-positional projection radiographs. In contrast, the GT method requires a complete set of multi-positional projection radiographs for each tomographic image. A recent review of both the GT and DXT methods is provided in J. Dobbins, D. Godfrey, Phys. Med. Biol. 48 (2003), R65–R106. This review discusses the prior art of the DXT mathematical reconstruction algorithms; these algorithms will be compared to the present invention later in this specification.

Although the initial development of DXT methods showed potential for clinical applications, the clinical deployment has been limited due to the relative immaturity of the digital x-ray image sensors. The image performance of earlier image intensifier tubes was limited in spatial resolution and detective quantum efficiency (DQE). In the late 1990s to present, however, the emerging technological developments in flat panel digital x-ray image sensors have enabled high performance digital x-ray imaging capability in a two-dimensional pixelated array format. These developments have enabled resurgence in DXT development, with ongoing clinical investigation of DXT imaging for chest radiography and mammography, for example. However, to date, the DXT method has still not seen widespread clinical deployment.

Portable X-ray Vents

In the last few years, the digital x-ray image sensor technology has advanced to the point where some of the sensors have become truly portable. Also, high-speed computing and digital display technologies have become available in lightweight, portable packages. One of the applicants is a co-inventor of such a unit.

Least Squares Techniques

Least squares type techniques (also referred to by names such as chi-squared fitting) are well known techniques for fitting large amounts of data to known functions.

What is needed are better DXT systems, especially a portable DXT radiographic systems for use in remote medical applications, such as emergency trauma or combat casualty care, for example. In addition, there is a growing need for a portable, low dose, DXT radiographic system that will provide detection and characterization of explosives devices in packages and luggage.

SUMMARY OF THE INVENTION

This invention provides the methods and devices for digital x-ray tomosynthesis. Tomographic and/or three-dimensional images of an object are obtained with an x-ray source and a digital x-ray image sensor. The source, object and sensor are positioned relative to each other and attenuation data is obtained for a large number of rays of x-radiation through the object. A special algorithm is provided to convert the data into images. To calculate the images the algorithm uses iterative processes with a least squares type technique but with generalized (as opposed to specific) functions. The algorithm solves for the functions which are the images. Preferred embodiments include a system having an x-ray point source with a cone of diverging x-rays, a two-dimensional digital x-ray image sensor, two linear translation stages to independently move both the x-ray source and the digital x-ray image sensor, two rotation mechanisms to rotate the two linear translation stages, a microprocessor to control the data acquisition, and a computer programmed with a special algorithm to calculate the tomographic images. A plurality of sets of digital data (representing x-ray algorithm images of an object) are acquired by the digital x-ray image sensor, with the x-ray source and the digital x-ray image sensor located at different positions and angles relative to the object. The digital data representing the x-ray attenuation images is stored in the computer. Special mathematical algorithms then compute multiple images of the object using the acquired digital data. These images could include multiple tomographic images, a three-dimensional image, or a multiple three-dimensional images.

Features of preferred embodiment of the present invention include: 1) technique for positioning of the x-ray source to reduce total number of digital projection radiographs as compared to prior art devices to minimizing total x-ray dose, and image reconstruction with reduced image aliasing artifacts; 2) positioning of the digital x-ray image sensor to increase the field of view; 3) special linear reconstruction algorithms providing image reconstruction of the tomographic images as well as determination; 4) computationally efficient image reconstruction algorithms to provide rapid image reconstruction; 5) applications of nonlinear techniques, such as wavelet transforms and filtering of the acquired data, in order to provide image reconstruction of tomographic slices that are sparsely surrounded by spatially "cluttered" image data and system configurations that permit the invention to be applied to portable units.

BRIEF DESCRIPTION OF THE DRAWINGS

FIGS. 6A(1) through 6C(2) are drawings that shows the optimal positioning of the x-ray image sensor for different positions of the x-ray source in order to maximize the field of view.

DETAILED DESCRIPTION OF PREFERRED EMBODIMENTS

Hardware

Figure 1:
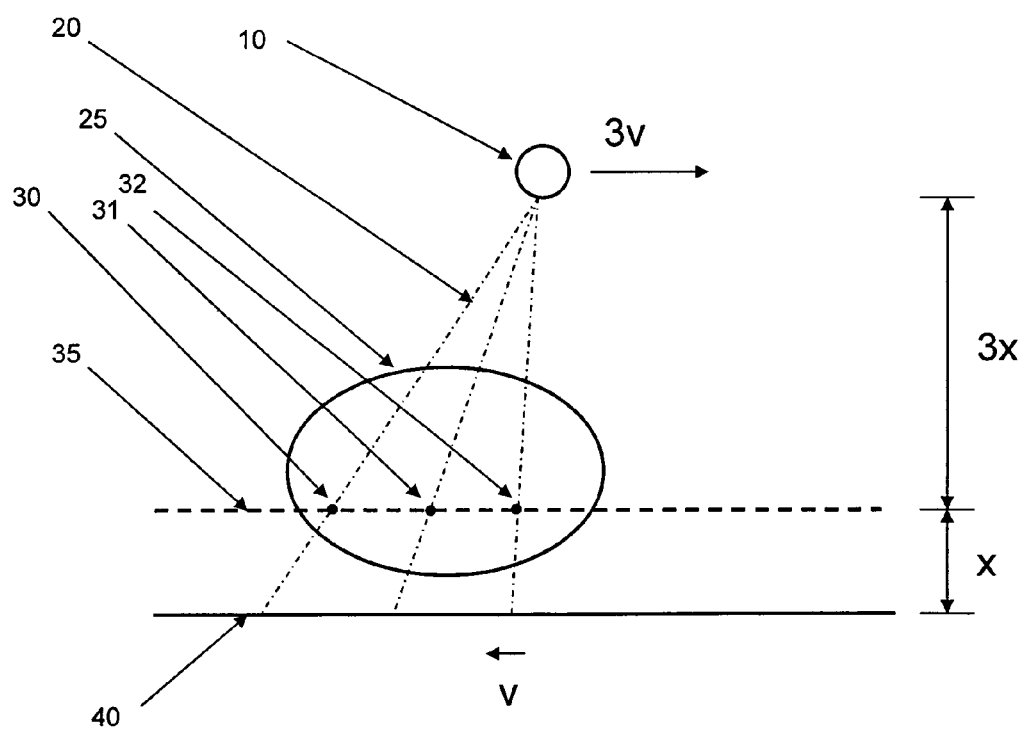
FIG. 1 is a drawing that shows the geometric tomography technique using co-moving x-ray source and x-ray film during x-ray exposure.
Figure 2:
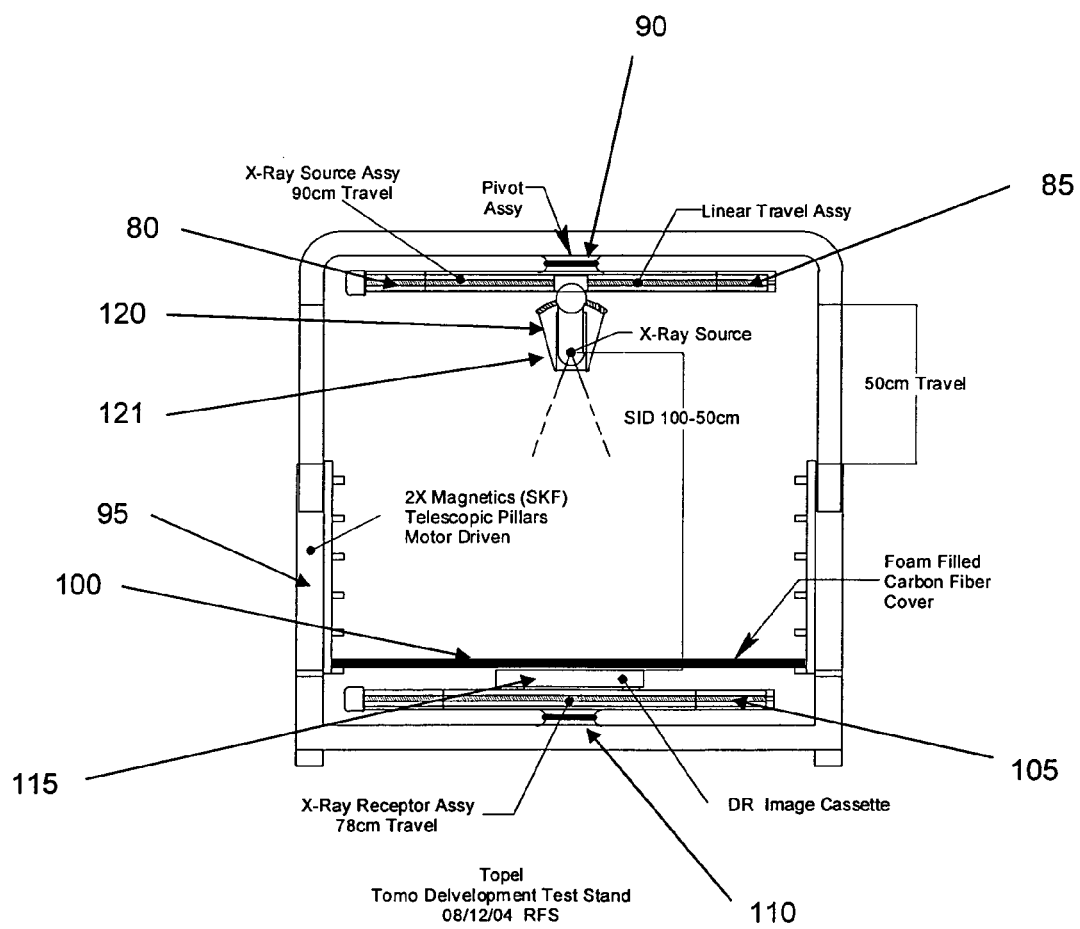
FIG. 2 is a drawing that shows the side view of the mechanical features of the preferred embodiment.

Preferred embodiments of the DXT system hardware are displayed in FIG. 2. X-ray source 120 is attached to linear translation stage 85 which is attached to pivot assembly 90. This enables the x-ray source 120 to be selectively positioned along a plane at the top of the DXT system so that x-ray source assembly 121 can be move left and right from its central position show in FIG. 1. In addition, the x-ray source 120 can be selectively tilted about pivot point 119 for each position of the x-ray source along the dimension of the translation stage 85, in order to direct the cone of x-rays directly at the object to be imaged. Digital x-ray image sensor 115 is positioned on linear translation stage 105 which is attached to pivot assembly 110. This enables the digital x-ray image sensor 115 to be selectively positioned along a plane at the base of the DXT system. The source-to-image distance (SID) is adjustable in the range of 50–100 cm by the use of telescopic pillars 95 supplied by SKF Magnetics with offices in Bethlehem, Pa. The object to be imaged is placed on platform 100 that is transparent to x-rays. Platforms can be placed at any of five vertical levels and then positioned vertically at different heights (0–50 cm) with pillars 95 relative to the digital x-ray image sensor 115.

The preferred x-ray sensor 115 is an indirect detection sensor based on a thin-film transistor (TFT) technology that involves the fabrication of a two-dimension array of amorphous silicon-based electronic circuit pixels on large (30 cm×40 cm, for example) glass sheets. The TFT array is sensitive to visible radiation (400 nm–700 nm). This array is coated or covered with a material that converts incident x-rays to visible light and the visible light is recorded by the pixelated TFT array and digitized to provide a two-dimensional digital image of the incident x-rays. Typical x-ray to light converters include gadolinium oxisulfide ($Gd_2O_2S$:Tb) phosphor screens or dendritic cesium iodide scintillator coatings. Preferred x-ray to light converters include high x-ray attenuation characteristics (PI-200 $Gd^2O^2S$:Tb, 436 microns thick, 200 mg/cm$^2$; Kasei Opthonix, for example), these converters provide very good detective quantum efficiency (DQE) and very good special resolution. Alternate sensor embodiments include direct detection x-ray sensors;

such as amorphous selenium coated TFT arrays, for example. Incident x-ray photons are converted directly into electronic charge in the amorphous selenium layer, and the charge is collected at each pixel. Indirect detection x-ray sensors available from Canon, Thales, and Varian and direct detection x-ray sensors are available from General Electric and Hologic.

The preferred x-ray source 120 features a tungsten non-rotating anode with a 50–160 kVp tube potential range, and a 0–0.5 mA tube current. A microprocessor subsystem controls the position of x-ray source 120 and x-ray sensor 115 by controlling translation stages 85 and 105 and rotation stages 90 and 110. The microprocessor subsystem also controls the technique factors (tube voltage, tube current, and exposure time) of x-ray source 120. The DXT system incorporate a computer and software to acquire, store, and display projection radiographs; provide digital tomosynthesis image reconstruction calculations; and display tomographic images.

Novel Features of the Invention

Figure 3:
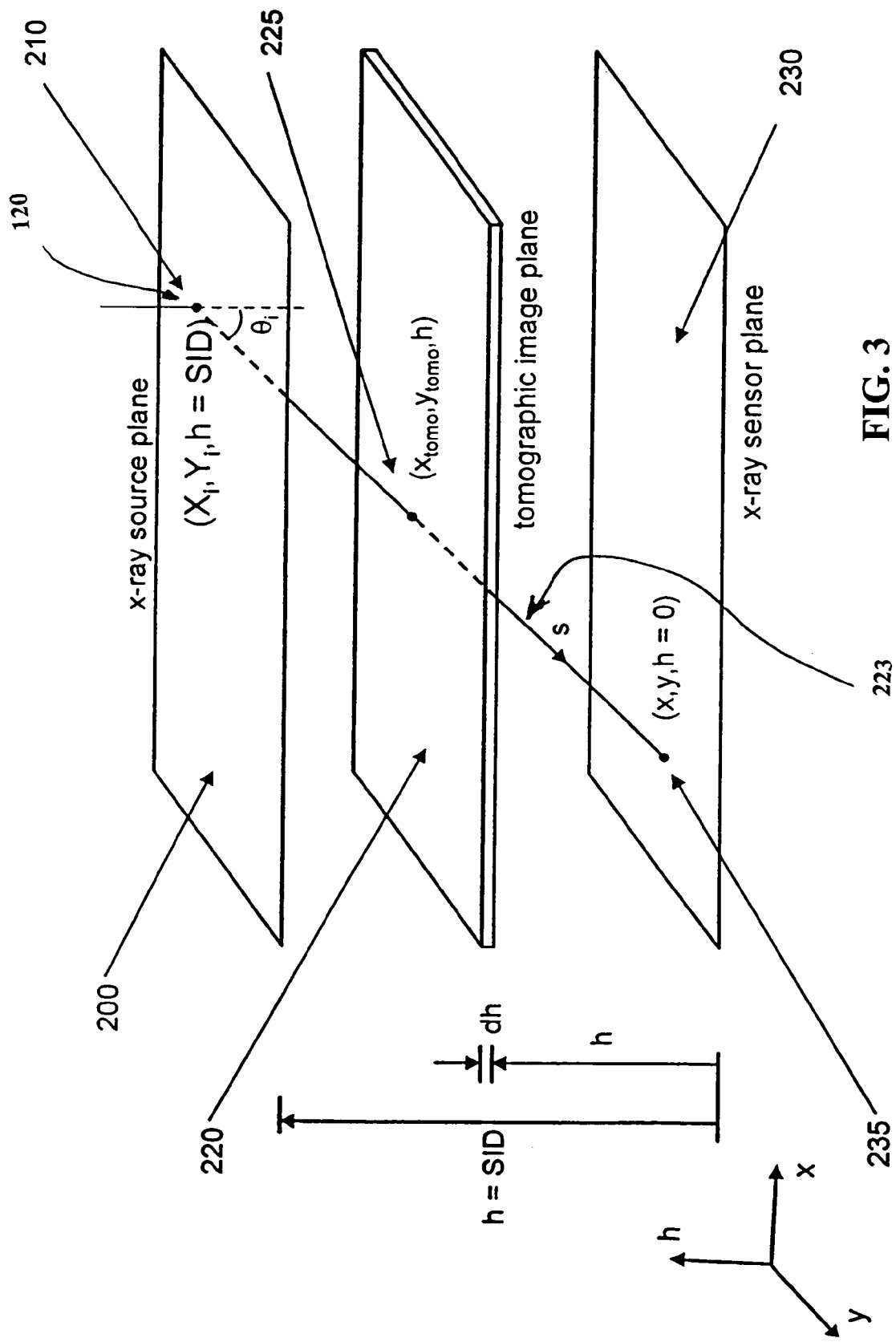
FIG. 3 is a drawing that shows a geometrical description of the parameters used in the image reconstruction algorithm.

The preferred geometrical arrangement for the invention is displayed in FIG. 3. The positioning of x-ray source 120 is constrained to positions 210 (i.e., $x_i$, $y_i$, h) on x-ray source plane 200, and the positioning of x-ray sensor 115 is constrained to x-ray sensor plane 230 that is parallel to x-ray sensor plane 200 at a distance h=SID. The system produces tomographic images located in tomographic image plane 220 that is parallel to x-ray sensor plane 120 at distances h and a tomographic slice thickness dh. A plurality of tomographic images are calculated, each image at different distances h from x-ray sensor plane 210. Typical X-ray 223 is emitted at angle (θ,φ) [representing dimensions (elevation, azimuth)] by x-ray point source 120 that is located at position ($X_i$, $Y_i$, h=SID) in x-ray source plane, and travels a straight line trajectory that intercepts tomographic image plane 220 at position ($x_{tomo}$, $y_{tomo}$, h) and is then incident on x-ray sensor 115, located at x-ray sensor plane 120, at pixel position (x,y, h=0).

Figure 4:
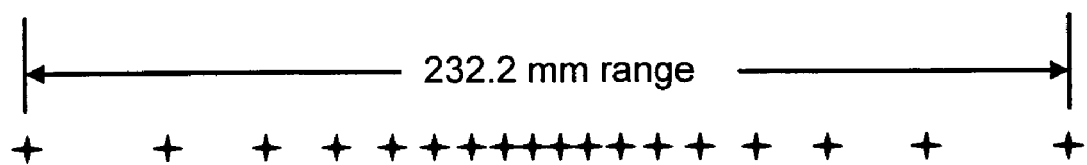
FIG. 4 is a drawing that shows the optimal x-ray source positions along one dimension.
Figure 5:
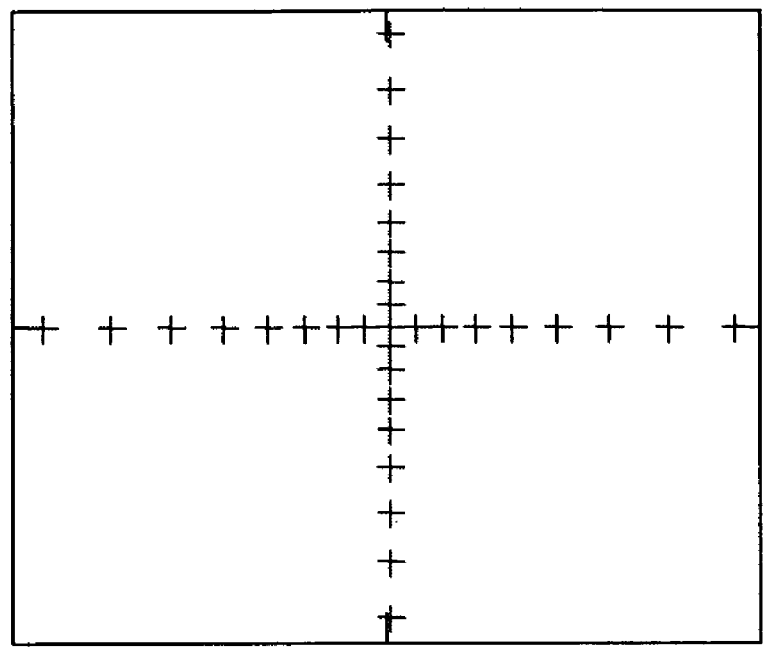
FIG. 5 is a drawing that shows the two-dimensional positioning of the x-ray source.

The primary objective of digital tomosynthesis is to provide an x-ray attenuation image that is isolated to a single tomographic slice, so that spatially varying x-ray attenuation from other slices does not clutter the image. A second objective is to help identify features by finding the three-dimensional positions of the features. Previous DXT methods have implemented a simple shift-and-add technique that basically emulates the motional blurring described by the GT method, in order to visualize the single image plane at the fulcrum of motion of the x-ray source and image sensor. We describe the important features of our method which include positioning of the source and sensor relative to the object being imaged and a special algorithm for constructing images using the acquired data:

1) Optimal positioning of the x-ray source: This feature describes a preferred total number of digital projection radiographs, and total x-ray dose to produce image reconstruction with minimal image aliasing artifacts. These constraints depend on aliasing and spatial frequency range considerations, as well as the source-to-image distance (SID).

a) Aliasing: There is a minimum preferred angular positioning step of the x-ray source required to discriminate planes for desired spatial frequencies of the image. This step is such that the spatial shift of the highest spatial frequency from the top slice to the bottom slice is approximately 1 line pair. If a larger minimum step were to be used, there would be some ambiguity in the reconstruction as to which plane the feature was in (known as aliasing) which would increase the noise in the image. For the preferred system, we specify $f_{max}$=1.5 lp/mm, object thickness=300 mm, which results in a minimum step of 2 milliradians (0.23 degrees).

b) Spatial Frequency Range: A large angular positioning range results in a reduction of the image slice thickness for the lowest spatial frequencies. The angular positioning range is approximately the ratio of this low spatial frequency to the image slice thickness. Very low spatial frequencies cannot be well localized without scanning through large angles. The preferred angular positioning range is 1.0 radian (57.32 degrees), depending on the features of interest.

c) Source-to-image distance (SID): The preferred SID is chosen based on geometrical requirements, clearance requirements, and spot size requirements. If a 600 micron diameter x-ray spot tube is used, then a reasonable specification of 200 micron blur requires a 3:1 ratio of SID to subject depth. This translates into a preferred SID=900 mm for a 300 mm typical subject. A 300 micron diameter spot tube will have lower x-ray exposure capability but places less constraints on the SID. From a geometrical perspective, there is a magnification effect for objects away from the detector, which becomes more extreme for small SIDs. A ratio of 2:1 magnification or less should cause little impact on the reconstruction process. The preferred range of SID is between 750 mm and 1000 mm.

d) One dimensional positioning of the x-ray source: The key to simultaneously resolving the constraints of aliasing and range is to let the positioning step length of the x-ray source be small near the center of the positioning range (so that small features do not alias) and larger as the tube moves away from the center (so that the low spatial frequencies are well localized). If constant sized steps were used, the number of image angles taken would be impractical. A preferred positioning of the x-ray source, in one scan dimension is displayed in FIG. 4. The positioning is symmetric around ($X_{center}$, $Y_{center}$), defined as the center of x-ray source plane 200, with 21 x-ray source positions, and a SID=900 mm. The positions of x-ray source 120 are described by $$X_i - X_{center} = \pm d\left[\frac{\exp(ia) - 1}{a}\right] \qquad \text{Eq. (1)}$$

where d=5 mm, a=0.15, and i=0, . . . , 10; so that the positions $X_i$-$X_{center}$=0, ±5.4 mm, ±11.7 mm, ±18.9 mm, ±27.4 mm, ±37.2 mm, ±48.7 mm, ±61.9 mm, ±77.3 mm, and ±95.1 mm. The total positioning range for the preferred embodiment is 2* 116.1 mm=232.2 mm and degrees.

e) Two-dimension positioning of the x-ray source: Most prior implementations of digital tomosynthesis so far have used positioning of the x-ray source in only one dimension, as shown in FIG. 4. While acceptable for some applications, there is a serious drawback, namely, it is impossible to localize the slice height of objects running parallel to the positioning direction. The best way around this is to position x-ray source 120 in two dimensions, thereby removing any sensitivity to object orientation. The preferred embodiment for this two dimension positioning, displayed in FIG. 5, is $$X_i - X_{center} = \pm d\left[\frac{\exp(ia)-1}{a}\right] \text{ and} \qquad \text{Eq. (2)}$$

$$Y_i - Y_{center} = \pm d\left[\frac{\exp(ia)-1}{a}\right]$$

where d=5 mm, a=0.15, and i=0, . . . , 9. Eq. (2) gives the positions $X_i-X_{center}$=0, ±5.4 mm, ±11.7 mm, ±18.9 mm, ±27.4 mm, ±37.2 mm, ±48.7 mm, ±61.9 mm, ±77.3 mm, ±95.1 mm, and ±116.1 mm, with the y-axis of x-ray source 120 positioned at $Y_{center}$; and positions $Y_i-Y_{center}$=0, ±5.4 mm, ±11.7 mm, ±18.9 mm, ±27.4 mm, ±37.2 mm, ±48.7 mm, ±61.9 mm, ±77.3 mm, and ±95.1 mm, with the x-axis of x-ray source 120 positioned at $X_{center}$. The total number of positions of x-ray source 120 is 41. The total angular positioning range is θ=2*arc tan(232.2 mm/900 mm)=0.52 radians=30 degrees.

f) X-ray Source Positioning Accuracy: The required accuracy of the translation stage is a fraction of the spot size of x-ray source 120. This translates to roughly 200 micron positioning accuracy for a spot size of 600 microns for x-ray source 120, which can be reasonably achieved.

2) Optimal positioning of the x-ray sensor: FIGS. 6A(1) and (2) show that the preferred x-ray sensor 115 is positioned, for each x-ray source 120 position, so that the field of view of the object is maximized. This is accomplished by positioning x-ray sensor 115 in a direction opposite to x-ray source 120 position so that a line 300 between x-ray source 120 and the center of x-ray sensor 115 has a virtual fulcrum of motion 310 that is approximately 20 cm above x-ray sensor 115; this provide a 30 cm field-of view. FIG. 6B(1) and (2) show that a 42 cm fulcrum of motion 310 only provides a 12 cm field of view and FIG. 6C(1) and (2) show that a 0 cm fulcrum of motion 310 only provides a 22 cm field of view.

3) Linear image reconstruction algorithm: A preferred reconstruction algorithm takes input digital projection radiograph image data of an object with the x-ray source at multiple positions and angles relative to the object, and transforms the input data into tomographic images. A number of techniques have been demonstrated to date, such as the simple shift-and-add approach and iterative techniques. We have developed an image reconstruction algorithm that we believe outperforms the other approaches while being computationally manageable.

a) Mathematical Description of Reconstruction Algorithm: The geometry of the mathematical problem is displayed in FIG. 3. X-ray point source 120 (STET) is positioned at different N separate positions 210 ($X_i,Y_i$); i=1, N in x-ray source plane 200 located at h=SID. The x-ray sensor is located in the x-ray sensor plane located at h=0. The The three-dimensional object that is imaged is represented by a scalar function d($x_{tomo}$, $y_{tomo}$, h) in the dimension of Hounsfield units we calculate d(xyh). The Hounsfield unit is the common metric for computer axial tomography (CAT) scan images. One Hounsfield unit equals a 0.1% difference in the density of water and the range of Hounsfield units is from –1000 (air) to 1000 (bone) with 0 Hounsfields as the density of water. The attenuation of x-rays directed along the line 223 (trajectory s) is given by $$A_i(s) = A_i\left[\int_0^s d(x_{tomo}, y_{tomo}, h)ds'\right] \qquad \text{Eq. (2)}$$

where ($x_{tomo}$, $y_{tomo}$) are the coordinates where the trajectory s crosses the tomographic plane at z=h. The functional form of $A_i(s)$ is nearly exponential and depends on the x-ray spectrum of the x-ray source. The coordinates $$(x_{tomo}, y_{tomo}) = \left(x\left[1 - \frac{h}{SID}\right] + \frac{hX_i}{SID}, y\left[1 - \frac{h}{SID}\right] + \frac{hY_i}{SID}\right) \qquad \text{Eq. (3)}$$

and the line element $$ds' = -\sec\theta_i(x,y)dh \text{ where} \qquad \text{Eq. (4)}$$

$$\sec\theta_i(x,y) = \sqrt{1 + \frac{(x-X_i)^2 + (y-Y_i)^2}{SID^2}} \qquad \text{Eq. (5)}$$

We can combine equations 2–5 and express the log of the attenuation of x-rays along the trajectory s from the x-ray source position ($X_i,Y_i$,h=SID) to the position (x,y,h=0) in the plane of the x-ray sensor as $$A_i(s) = \qquad \text{Eq. (6)}$$

$$A_i\left[\int_0^{SID} d\left[x\left(1 - \frac{h}{SID}\right) + \frac{hX_i}{SID}, y\left(1 - \frac{h}{SID}\right) + \frac{hY_i}{SID}, h\right]\sec\theta_i(x,y)dh\right]$$

The log of the pixelated digital x-ray images acquired by the digital x-ray image sensor are represented by $$m_i(x,y) = m0_i(x,y) + n_i(x,y) \qquad \text{Eq. (7)}$$

where $$m0_i(x,y) = w(x,y)A_i(s)psf(x,y) \qquad \text{Eq. (8)}$$

are the noise-free measurements for each the N source positions ($X_i,Y_i$); i=1, N, $n_i(x,y)$ is the noise, $w_i(x,y)$ is the white field image acquired during calibration, and psƒ(x,y) is the point spread function. In equation 8, the symbol ⊗ denotes a two-dimensional convolution operation over variables (x,y). The white field will be measured directly for each x-ray source position and not calculated so as to calibrate other effects such as angular variations of the x-ray source pattern and x-ray anti-scatter grid effects, for example. By combining equations 6 and 8, we have $$m0_i(x,y) = w(x,y) \qquad \text{Eq. (9)}$$

$$A\left[\sec\theta_i(x,y)\int_0^{SID} d\left[x\left(1 - \frac{h}{SID}\right) + \frac{hX_i}{SID}, y\left(1 - \frac{h}{SID}\right) + \frac{hY_i}{SID}, h\right]dh\right] \otimes psf(x,y)$$

We need to invert equation 9 to express the tomographic slice image data d(x,y,h) in terms of the acquired noise free data m0(x,y). We invert equation 9 by minimizing the following generalized chi-squared function versus the function d($x_{tomo}$, $y_{tomo}$, h)

$$\chi^2 = \sum_i \int\int (m_i(x_o, y_o) - m0_i(x_o, y_o))[(n(x_0, y_0)n(x_1, y_1))_{avg}]^{-1}$$
$$(m_i(x_1, y_1) - m0(x_1, y_1))dx_o dy_o dx_1 dy_1 +$$
$$\varepsilon \int\int d(x, y, h)^2 dx dy dh \quad \text{Eq. (10)}$$

where e is a regularization parameter chosen so that the first term averages 1 per measurement and m0 is implicitly a function of d.

We simplify equation 9 by first remapping d to the function D $$d(x, y, h) = D\left(x\frac{SID}{SID-h}, y\frac{SID}{SID-h}, h\frac{SID}{SID-h}\right)\left(\frac{SID}{SID-h}\right)^2 \quad \text{Eq. (11)}$$

and changing variables $$z = \frac{SID}{SID-h}h \quad \text{Eq. (12)}$$

The integrals in equations 6 and 10 are then transformed to $$\int_0^h d\left[x\left(1 - \frac{h}{SID}\right) + \frac{hX_i}{SID}, y\left(1 - \frac{h}{SID}\right) + \frac{hY_i}{SID}, h\right]dh = \quad \text{Eq. (13)}$$
$$\int_0^h D\left[x + \frac{X_i h}{SID-h}, y - \frac{Y_i h}{SID-h}, \frac{SIDh}{SID-h}\right]\left(\frac{SID}{SID-h}\right)^2 dh =$$
$$\int_0^\infty D\left(x + \frac{X_i z}{SID}, y + \frac{Y_i z}{SID}, z\right)dz$$

and $$\int\int d(x, y, h)^2 dx dy dh = \quad \text{Eq. (14)}$$
$$\int\int D\left(x\frac{SID}{SID-h}, y\frac{SID}{SID-h}, \frac{SIDh}{SID-h}\right)^2\left(\frac{SID}{SID-h}\right)^4 dx dy dh =$$
$$\int\int D\left(x, y, \frac{SIDh}{SID-h}\right)\left(\frac{SID}{SID-h}\right)^2 dx dy dh =$$
$$\int\int D(x, y, z)^2 dx dy dz$$

Equation 9 is then expressed as $$m0(x, y) = w_i(x, y)A\left[\sec\theta_i(x, y)\int_0^\infty D\left(x + \frac{X_i z}{SID}, y + \frac{Y_i z}{SID}, z\right)dz\right] \otimes psf(x, y) \quad \text{Eq. (15)}$$

and equation 9 is expressed as $$\chi^2 = \sum_i \int\int (m_i(x_o, y_o) - m0_i(x_o, y_o))[(n(x_0, y_0)n(x_1, y_1))_{avg}]^{-1} \quad \text{Eq. (16)}$$
$$(m_i(x_1, y_1) - m0(x_1, y_1))dx_o dy_o dx_1 dy_1 +$$
$$\varepsilon \int\int D(x, y, z)^2 dx dy dh$$

The noise correlation is generated from the noise power spectrum (NPS) function $$(n_i(x_0, y_0)n_i(x_1, y_1))_{avg} = \int NPS(x_0-x, y_0-y, x_1-x, y_1-y, x, y) dx dy \quad \text{Eq. (17)}$$

We assume at the noise is slowly varying over the region integrated (a common approximation), so we can approximate $$\int NPS(x_o - x, y_o - y, x_1 - x, y_1 - y, x, y) dx dy = \quad \text{Eq. (18)}$$
$$nps(x_o - x_1, y_o - y_1)\sqrt{noise_i(x_o, y_o)}\sqrt{noise_i(x_1, y_1)}$$

where nps is the noise power spectrum correlation function normalized to 1 at 0 lp/mm, and "noise" is more slowly varying 0 lp/mm noise. The assumption restated is that the noise varies too slowly to matter much which parameter x is used in its argument.

We next define an "integrated Hounsfield" measurement M and its noise free version M0, which is a transform of the raw measurement m0

$$M0_i(x, y) = \int D(x + \alpha z, y + \beta z, z)dz \quad \text{Eq. (19)}$$
$$= \frac{1}{\sec\theta_i(x, y)}A^{-1}\left[\left(\frac{m0_i(x, y)}{w_i(x, y)}\right) \otimes (psf^{-1}(x, y))\right]$$

$$M_i(x, y) = \frac{1}{\sec\theta_i(x, y)}A\left[\left(\frac{m_i(x, y)}{w_i(x, y)}\right) \otimes [psf^{-1}(x, y)]\right] \quad \text{Eq. (20)}$$

By using a first order Taylor expansion (which is appropriate for the low noise regime we will operate in), and bringing the slowly varying white field term $w_i(x,y)$ outside of the convolution, the difference of M and M0 is a transformed noise term $$M_i(x, y) - M0_i(x, y) = \quad \text{Eq. (21)}$$
$$\frac{(m_i(x, y) - m0_i(x, y)) \otimes (psf^{-1}(x, y))}{\sec\theta_i(x, y)w_i(x, y)A'(M_i(x, y)\sec\theta_i(x, y))}$$

where $A'(v) = \frac{d}{dv}A(v)$.

Notice that the term in the denominator $w_i(x,y)A'(M_i(x,y)\sec\theta_i(x,y))$ is the derivative of the signal versus thickness which we will call "dsignal" and which can calculated or measured. Using this expression $$m_i(x,y)-m0_i(x,y)=[(M0_i(x,y)-M_i(x,y))\text{dsignal}_i(x,y)\sec\theta_i(x,y)]\text{psf}(x,y) \quad \text{Eq. (22)}$$

We can now express the optimization function (equation 16) as $$\chi^2 = \sum \left[\left((M_i - M0_i)\frac{\text{dsignal}_i\sec\theta_i}{\sqrt{\text{noise}_i}}\right) \otimes \text{psf} \otimes (\text{nps}^{-1}) \otimes \right.$$
$$\left. \text{mtf} \otimes \left[(M_i - M0_i)\frac{\text{dsignal}_i\sec\theta_i}{\sqrt{\text{noise}_i}}\right]\right]_{x=0,y=0} + $$
$$\varepsilon \int\int D(x,y,z)^2 dx\,dy\,dz \quad \text{Eq. (23)}$$

The convolution in the middle is, by definition, the detective quantum efficiency $$\text{dqe} = \text{psf}(\text{nps}^{-1})\text{psf} \quad \text{Eq. (24)}$$

We define the ratio $$\frac{\text{noise}}{\text{dsignal}^2} = \Delta t2 \quad \text{Eq. (25)}$$

which is the "thickness noise" squared. Since noise is a strong function of thickness, and a weak function of angle, we can treat $\Delta t2$ as a function only of thickness. This function, like dsignal, can be calculated or measured.

For simplicity, we define a noise function $$\sigma_i(x,y) = \frac{\sqrt{\text{noise}_i(x,y)}}{\text{dsignal}_i(x,y)}\sec\theta_i(x,y)^{-1}$$
$$= \sec\theta_i(x,y)^{-1}\sqrt{\Delta t2(M_i(x,y)\sec\theta_i(x,y))} \quad \text{Eq. (26)}$$

and equation 23 is expressed as $$\chi^2 = \sum_i \left[\left(\frac{M_i - \int D(x+\alpha_i z, y+\beta_i z, z)}{\sigma_i(x,y)}\right) \otimes \text{dqe} \otimes \right.$$
$$\left. \left(\frac{M_i - \int D(x+\alpha_i z, y+\beta_i z, z)}{\sigma_i(x,y)}\right)\right]_{x=0,y=0} +$$
$$\varepsilon \int\int D(x,y,z)^2 dx\,dy\,dz \quad \text{Eq. (27)}$$

We can solve equation 27 by calculating the derivative of $\chi^2$ versus $D(x_0,y_0,z_0)$ and calculating where this derivative equals 0

$$0 = \sum_i \left[ \quad \text{Eq. (28)}\right.$$

$$\left.\left(\left(\frac{\int D(x+\alpha_i z, y+\beta_i z, z)dz}{\sigma_i(x,y)}\right) \otimes \text{dqe}\right)\frac{1}{\sigma_i(x,y)}\right]_{x=x_o-\alpha_i z, y=y_o-\beta_i z}$$
$$+ \varepsilon D(x_o, y_o, z)$$

The problem with this expression is that D is a continuous variable of z, and divisions into z-slices will lead to inaccuracy and/or increased computational burden. There is a solution to this problem, however, which is to let D be defined from a generator that is discrete $$D(x,y,z) = \sum_j G(x - \alpha_j z, y - \beta_j z, z) \quad \text{Eq. (29)}$$

Then equation 28 becomes $$0 = \sum_i \left[\left(\left(\frac{\int \sum_j G(x - \alpha_j z + \alpha_i z, y - \beta_j z + \beta_i z)dz - M_i}{\sigma_i(x,y)}\right) \otimes \text{dqe}\right)\right.$$
$$\left.\frac{1}{\sigma_i(x,y)}\right]_{x=x_o-\alpha_i z, y=y_o-\beta_i z} + \varepsilon \sum_i G(x_o - \alpha_i z_o, y_o - \beta_i z_o) \quad \text{Eq. (30)}$$

Equation 30 can only be true if the individual elements in the i-summation are identically equal to zero $$0 = \left(\left(\frac{\int \sum_j G(x - \alpha_j z + \alpha_i z, y - \beta_j z + \beta_i z)dz - M_i}{\sigma_i(x,y)}\right) \otimes \text{dqe}\right)$$
$$\frac{1}{\sigma_i(x,y)} + \varepsilon G_i(x,y) \quad \text{Eq. (31)}$$

We can simplify equation 31 further by defining a function C as $$C_{ij}(x,y) = \int_0^{z_{max}} \delta[x + (\alpha_i - \alpha_j)z, y + (\beta_i - \beta_j)z]dz \quad \text{Eq. (32)}$$

In equation 31, $z_{max}$ is determined by the height of the object that is imaged, and the integral excludes absorption below the detector or above $z_{max}$ in the solution. Equation 31 can be expressed as $$\text{dqe} \otimes \left(\frac{M_i}{\sigma_i}\right) = \text{dqe} \otimes \left(\frac{C_{ij} \otimes G_j}{\sigma_i}\right) + \varepsilon\sigma_i G_j \text{ (sum over } j) \quad \text{Eq. (33)}$$

This is the final equation to be solved for G, then we get D from G and finally d from D. If s were constant, then equation 33 could be inverted using Fourier transforms because the convolutions become products $$\Im(\text{dqe})\Im(M_i) = \Im(\text{dqe})\Im(C_{ij})\Im(G_j) + \varepsilon\sigma_i^2\Im(G_i) \quad \text{Eq. (34)}$$

where $\Im$ denotes a Fourier transform. Equation 33 is then expressed as $$\Im(G_i) = (\Im(dqe)\Im(C_{ij}) + \epsilon\sigma_i^2\delta_{ij})^{-1}\Im(dqe)\Im(M_i) \quad \text{Eq. (35)}$$

In equation 35, the inverses are performed individually over each spatial frequency. Note that these inverse matrices can be computed once and stored as a look-up table for improved computational speed. The stored data is required for each noise level and each value of $z_{max}$, so this data will require a large storage capacity. The technique that we use to solve equation 33 for a non-constant s involves treating the problem in multiple iterations with a constant $\sigma_{trial}$, solving equation 33 using the Fourier transform method (equation 34), calculating an error term, then iterating by reconstructing for the error term but using successively different values for the trial $\sigma$ value $\sigma_{trial}$. First calculate the error term $$\text{error} = dqe \otimes \left(\frac{M_i}{\sigma_i}\right) - dqe \otimes \left(\frac{C_{ij} \otimes G_j}{\sigma_i}\right) + \epsilon\sigma_i G_j \quad \text{Eq. (36)}$$

Then, invert the error term using a constant $\sigma$ $$dqe(C_{ij}\Delta G_i) + \epsilon\sigma_{trial}^2 \Delta G_i = \text{error} \quad \text{Eq. (37)}$$

Then, update the reconstructed generator coefficients $$G_i \leftarrow G_i + \Delta G_i \quad \text{Eq. (38)}$$

Then repeat with a different value of $\sigma_{trial}$. Eventually, the "error" becomes sufficiently small and we have our solution. We start with the largest value s for s, and then gradually decrease. Boundary conditions are handled by reflection conditions with tapering. The minimization function in this terminology is $$\chi^2 = \sum_i \left[\left(\frac{C_{ij} \otimes G_j}{\sigma_j} - \frac{M_i}{\sigma_i}\right) \otimes dqe \otimes \left(\frac{C_{ik} \otimes G_k}{\sigma_i} - \frac{M_i}{\sigma_i}\right)\right]_{x=0, y=0} + \epsilon(G_k \otimes C_{kj} \otimes G_j)\bigg|_{x=0, y=0} \quad \text{Eq. (39)}$$

So, the first term should equal (# of tube positions)×(# of pixels) when $\epsilon$ is set correctly.

To summarize, the steps are:
1) Transform the measurements m into the "integrated Hounsfield" form M
2) Repeat on:
   a. Calculate error term using non-constant s
   b. Select trial value strial
   c. Invert the error term with strial
   d. Update G
   e. Change strial
3) For a given slice selection, calculate D from G
4) Calculate d from D b) Computational Description of Reconstruction Algorithm This section provides the computational flow chart for the linear image reconstruction algorithm.

Raw data $mraw_i(x,y)$:
Data taken over all of the pixels, one shot for each tube location i. Nominal 41 tube locations, 2304 by 3072 pixels.

Dead pixel map dead(x,y):
Map of dead pixels, assumed constant for all i. If not, then must have a map for each i.

Binning function Bin(image,binsize):
Bins image data into N×N units. Nominal choices are N=4 (fine) and N=8 (coarse).

Compute binned raw data $mbin_i(x,y)$:

$$mbin_i(x,y) = \text{Bin}(mraw_i(x,y)*\text{dead}(x,y), N)/\text{Bin}(\text{dead}(x,y), N)$$

Dark field dark(x,y):
Dark field, assumed constant for all i. This assumption must be verified, may not be constant.

White field $white_i(x,y)$:
White field, definitely not constant vs. i, due to geometrical, grid, and other effects. Needs to be recalibrated every time tube settings are changed, either in output or position.

$white_i(x,y) = mbin_i(x,y) - \text{dark}(x,y)$ for an exposure with no subject (or a small amount of plastic plate).

Compute calibrated measurements $mcal_i(x,y)$:

$$mcal_i(x,y) = (mbin_i(x,y) - \text{dark}(x,y))/white_i(x,y)$$

Linearization calibration:
Compute $mcal_i(x,y)$ for various thicknesses t of water equivalent plastic plate, to give $mthick_i(x,y,t)$. Fit to the following function:

$$mthick_i(x,y,t) = C0_i(x,y) * \exp\left(t*(C1_i(x,y) + C2_i(x,y)*t)/(C3_i(x,y) + t)\right)$$

where C0, C1, C2, and C3 are slowly varying functions, probably a low order polynomial fit in x and y for each i.

Linearize the measurement:

$$mlin_i(x,y) = \{-C1 + \ln(mcal/C0) + [(\ln(mcal/C0) - C1)^2 + 4*C2*C3*\ln(mcal/C0)]^{1/2}\}/(2*C2)$$

where I have dropped the (x,y) and i notation for simplicity.

This parameter was called $M_i$ in solver algorithm write-up. The $1/\sec\theta_i(x)$ term in the write up is implicitly included in our linearization calibration because we use flat plates, which already have the effect built in.

Secant function used to derive $\sigma$:
Let source be at $(xs_i, ys_i, SID)$ and detector be at $(x, y, 0)$ then $\sec\theta_i(x,y) = [(xs-x)^2 + (ys-y)^2 + SID^2]^{1/2}/SID$ (the ratio of pixel distance from source to SID)

Noise function:
Functional relationship that estimates noise from thickness of water traversed, found by modeling:

$$\Delta t2e(t) = 1.487*10^{-5} \text{ mm}^4 * \exp([(t/4.385 \text{ cm})*38.6 \text{ cm} + (t/5.481 \text{ cm})*t]/[38.6 \text{ cm} + t])/(\text{pixel area})$$

The output has units of length$^2$, which corresponds to the error squared of the length estimate.

Compute Sigma:

$$\sigma_i(x,y) = \{\Delta t2e[mlin_i(x,y)*\sec\theta_i(x)]\}^{1/2}/\sec\theta_i(x)$$

This is the estimate of the error in $mlin_i(x,y)$. It should be very close to a computation of the variance from the region around each pixel for uniform subjects, and can be checked in this way.

As an alternative, we can try using a 3×3 nearest neighbor box and computing the variance within this box as an estimate for $\sigma_i(x,y)$. The output of this method should be clipped on the low side by a minimum value.

Pick eps:

This is a global constant parameter that determines how smooth the solution is. We will try reconstructions for different values until we understand what is preferable.

Compute the $C_{i,j}(k_x,k_y)$ Cholesky matrices:

These will be described separately, as it is the most involved portion of the algorithm.

Generators:

We will compute generators $G_i(x,y)$ as the output to the main algorithm, which is then put into a simple quick slice algorithm to recover the slice image. The generators are computed on an array the size of mbin, but are imbedded in a larger padded array, and use reflection or zero padding as boundary conditions.

Height:

The height from the detector is described by h, but the algorithm uses a modified height variable that I have called z, but will start calling $z_{eff}$ to prevent confusion. The relationship is as follows:

$z_{eff}=(SID*h)/(SID-h)$, with inverse $h=(SID*z_{eff})/(SID+z_{eff})$

Pivot point:

We use $h_{max}$ to denote the maximum object height from the detector. The algorithm assumes that there is nothing above this height. The corresponding $z_{max}=(SID*h_{max})/(SID-h_{max})$. The pivot point is placed at $h_{piv}=1/(2/h_{max}-1/SID)$. The corresponding $z_{piv}=z_{max}/2$.

Tube angle parameters

Each tube position has angles ($\Theta x_i$ and $\Theta y_i$ associated with it. The formula for these angles is:

$\Theta x_i=xs_i/SID$, $\Theta y_i=ys_i/SID$.

Slice image:

The images are first computed for a scaled slice that we call D:

$D(x,y,z_{eff})=\text{sum}_i\{G_i[x-\Theta x_i*(z_{eff}-z_{piv}), y-\Theta y_i*(z_{eff}-z_{piv})]\}$ Or in other words, the generator images are shifted by an amount that depends on height, then added together. The value of $z_{eff}$ given height is described above.

To recover the actual image $d(x,y,h)$, we must zoom and scale D:

$d(x,y,h)=D(x*\text{zoom}, y*\text{zoom}, z_{eff})*\text{zoom}^2$, where $\text{zoom}=SID/(SID-h)=z_{eff}/h$.

This removes the geometrical magnification effect.

We are ignoring the DQE effects for this first version of the algorithm.

Computing the generators:

The following is iterated:

First compute an error value:

$err_i(x,y)=m\text{lin}_i(x,y)-\text{sum}_j\{C_{ij}(x,y)G_j(x,y)\}-\text{eps}*\sigma_i(x,y)^2*G_i(x,y)$ The error is computed over the detector area.

The convolution operation will be described later. The convolution requires that the array be imbedded in a larger working area, and before the convolution takes place the data is padded either by reflection or just zeroing outside the detector area. The choice of boundary conditions must be the same as that used to generate the slice images.

Next invert this error value:

$\Delta G_i(x,y)=[C_{ij}(x,y)+\text{eps}*\sigma 0^2*\delta(x,y)*\delta_{ij}]^{-1}err_i(x,y)$ Where $\sigma 0$ is a constant, at least for a particular iteration. Then $G_i(x,y) \leftarrow G_i(x,y)+\Delta G_i(x,y)$ Again, this is computed over the detector area.

Each iteration can either use the same choice for $\sigma 0$ or can vary to improve convergence. A good starting value is the maximum of $\sigma_i(x,y)$. The total rms of $[err_i(x,y)/\sigma_i(x,y)]$ is used to decide if convergence is adequate.

Convolution operation:

In order to efficiently compute the forward and backward convolutions while minimizing data storage, a number of complications must be introduced:

1) The convolutions, as is usual are computed using FFT's
2) Since the matrix operations take place in Fourier space, $C_{ij}(x,y)$ is never actually computed or stored but rather $C_{ij}(k_x,k_y)$.
3) In Fourier space the convolutions become just simple matrix multiplications.
4) Since the generator functions are real, and their Fourier transform are symmetrical, a normal FFT has a factor of 2 redundancy. We therefore use a 2d Real FFT instead.
5) Due to the fact that $C_{ij}(x,y)$ is real, $C_{ij}(k_x,k_y)$ is symmetrical. We therefore only need to compute for half of the spatial frequencies, say $k_x \geq 0$.
6) Since we picked the pivot point $z_{piv}$ at exactly half of $z_{max}$, the $C_{ij}(x,y)$ turn out to be symmetrical (in x,y), and therefore $C_{ij}(k_x,k_y)$ is real.
7) The $C_{ij}(k_x,k_y)$ are also symmetrical, and in fact positive definite, in i,j. The positive definiteness follows from the definition of C, which will be discussed later. This allows C to be factored into a Cholesky decomposition, that is into a product of a lower triangular matrix L with itself $C=L*L^T$.
8) Only L is stored, and only the triangle of data values are saved and not the zeros.
9) To be more precise, we use $L*L^T=C_{ij}(k_x,k_y)+\text{eps}*\sigma 0^2*\delta_{i,j}$
10) In the forward operation we need to subtract $\sigma 0^2$ back out from the $\sigma_i(x,y)^2$ because we added it into the Cholesky matrices
11) The inverse operation can be computed almost as efficiently as the forward operation due to the properties of Cholesky matrices. Therefore we do not need to save separate matrices for each operation.
12) We need to write a special code to take the packed L matrices and perform the forward and inverse vector multiply operation. This is pretty easy, I will write it up.
13) We need to get a Real FFT code and implement it. A site called fftw.org seems to have this for free, but we will need to change it to single precision.
14) The FFT's use padded arrays, which need to approximately add at least the size of the convolution kernels of $C_{ij}(x,y)$. The array plus padding also must be a nice size for the FFT, such as a power of 2 times some small prime number (2,3,5).
15) The padding rules will have to be evaluated, but either zero padding or reflection padding will probably be best. It should make the most difference when the subject is sticking off the edge.

c) Numerical operation count: This section provides computational operation count as follows:
   Assumptions: 41 measurements, each with 2000×2000 pixels, and reconstruct 20 slices
   Input FFT's: 28*10^9 real multiplies
   Matrix operations: 13*10^9 real multiplies
   Output FFT's: 14*10^9 real multiplies
   Total: 55 Gops
   The computation time is therefore 1 min on a 1 Gflop processor. Note the assumptions are conservative and much faster processing times are possible with smaller data sets.
d) Rationale for image reconstruction algorithm: The preferred linear image reconstruction algorithm, described by the $\chi^2$ minimization equation (10), is derived using equation (18.4.9) and (18.4.11) in Numerical Recipes in Fortran 77; the Art of Scientific Computing", Chapter 18.4 "Inverse Problems and the Use of A Priori Knowledge", Cambridge University Press, pg. 795–799 (1986–1992).

$$\chi^2 = \sum_{ij}\left[c_i - \sum_\mu R_{i\mu}u(x_\mu)\right]S_{ij}^{-1}\left[c_j - \sum_\mu R_{j\mu}u(x_\mu)\right] + \lambda\sum_\mu u^2(x_\mu) \quad \text{Eq. (40)}$$

where $c_i \equiv m_i(x_0, y_0)$ are the measurements, $$\sum_\mu R_{i\mu}u(x_\mu) \equiv m_o(x_o, y_o)$$

are the unknown model data convolved with the response function of the measurements system, and $S_{ij} \equiv (n(x_0,y_0)n(x_1,y_1))_{avg}$ is the covariance noise function. Eq. (40), and therefore Eq. (10), is the functional generalization of the conventional chi-squared fitting algorithm that fits a straight line, for example, to a measured set of data points $(x_i, y_i)$; the best fit seeks to minimize the function (Eq. 15.1.5 in Numerical Recipes)

$$\chi^2 = \sum_i \left(\frac{y_i - y(x_i; a_1, \ldots, a_m)}{\sigma_i}\right) \quad \text{Eq. (41)}$$

where $\sigma_i$ is the uncertainty, or noise, associated with each data point. The fit is constrained to functional form (straight line or quadratric function, for example) and constants $(a_1, \ldots, a_m)$ are determined by the fit. Equations (40) and (10) seek to minimize an equivalent $\chi^2$ function but do not constrain the problem to a specific functional form. The optimal three-dimensional function $d(x_{tomo}, y_{tomo}, h)$, representing the tomographic images, is calculated by the minimization routine. Equation (40), and equation (10), is constrained by the second term that imposes a certain amount of "smoothness" to the solution, depending on the value of the regularization paerameter $\lambda$ (or $\epsilon$). The preferred embodiment uses a value $\epsilon=0.01$ for regularization parameter.

e) Non-linear reconstruction algorithms: We assume that optimal reconstruction algorithm is the best that can be done with no assumptions about the nature of the subject being imaged. The proposed DXT system incorporates non-linear algorithms that incorporate additional information:
   Minimization of the effect of overlaying tissue by tailoring sidelobe artifacts to be lower from regions with strong features and higher from featureless areas. Techniques developed for sonar and radar may be applicable. These basically work by weighing projections more heavily which pass through "windows" in the subject.
   Sharpening of slice thickness by "concentrating" features. Some spatial frequencies can be located in depth better than others, so we can increase the probability that a feature at one spatial frequency lies together with the same feature measured at a different spatial frequency.
   Imposing an outer boundary of the subject, so we can numerically constrain zero tissue outside of this boundary.

Simulation of the Reconstruction Algorithm

Figure 7:
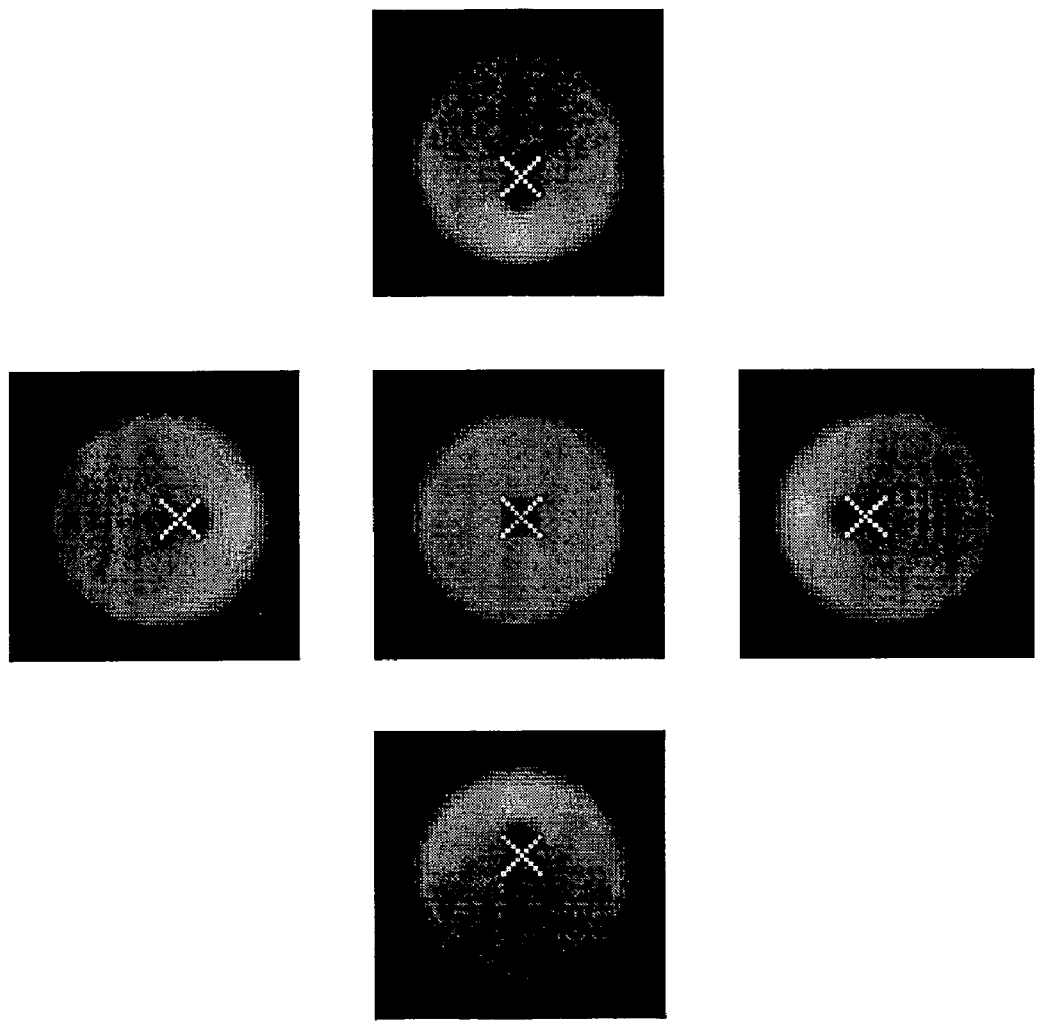
FIG. 7 is a computer simulation that shows five digital projection radiographs of a thick walled cone with an "x" in the middle, each radiograph simulated with the x-ray source at a different position.
Figure 8:
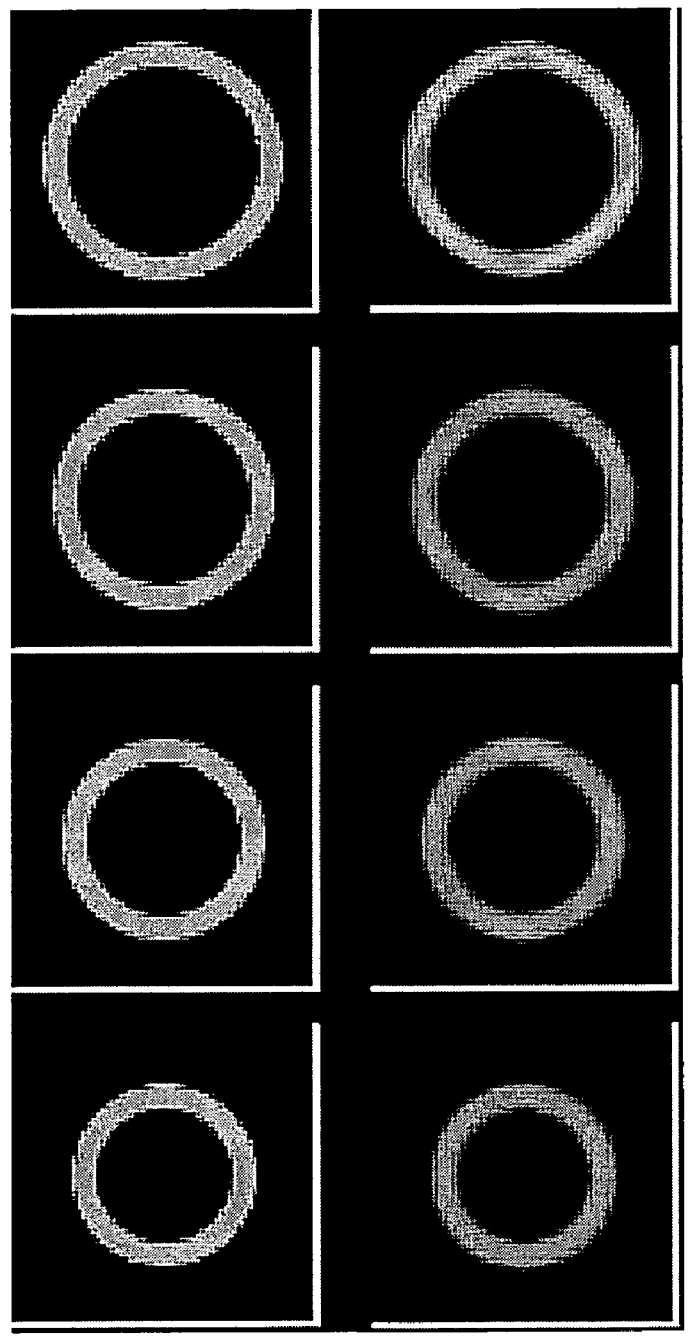
FIGS. 8–10 are twelve reconstructed tomographic images of the thick walled cone with an "x" in the middle.
Figure 9:
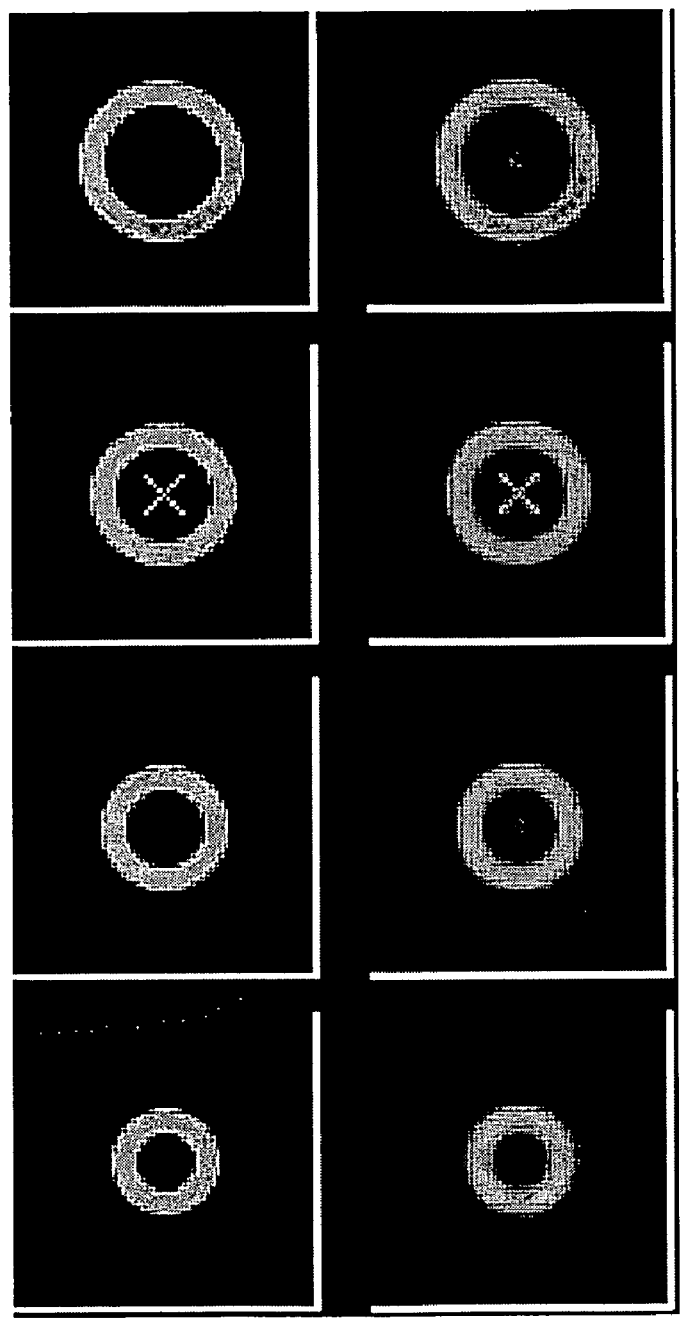
Figure 10:
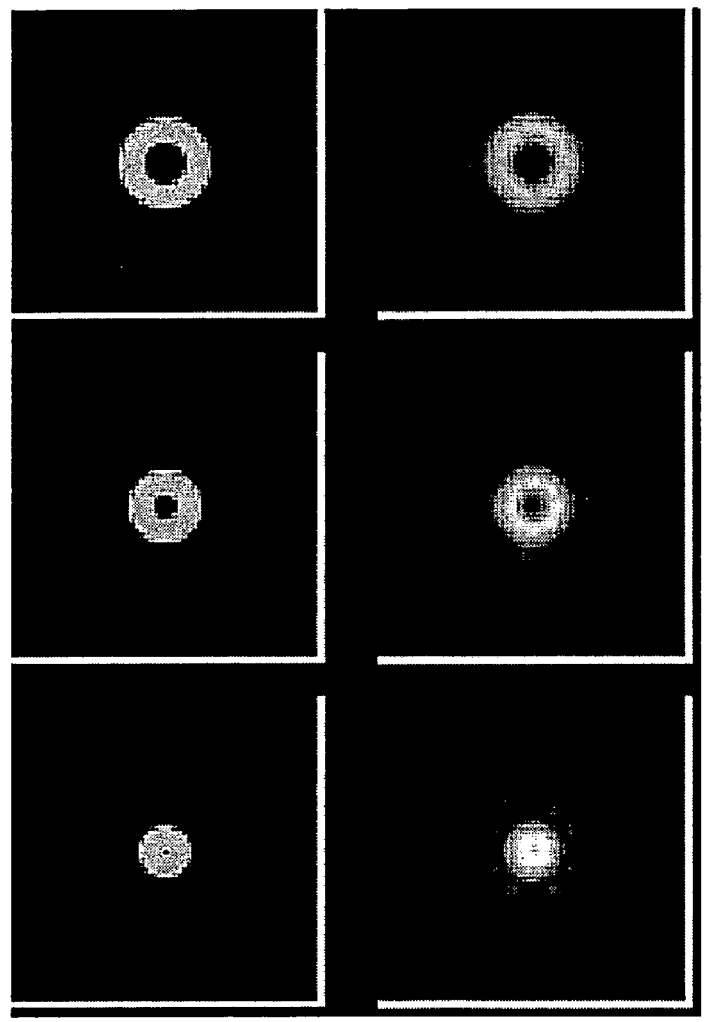

A computer simulation of a preferred linear reconstruction algorithm is displayed in FIGS. 7 and 8. The object is a thick walled cone with an "x" in the very center of the object; this object was taken to be a combination of low and high spatial frequencies to demonstrate various aspects of the algorithm, and present a reasonably challenging case. The simulated cone is made up of 100 separate slices to ensure accuracy. Multiple digital projection radiographs of the cone viewed from various positions of the x-ray source 120 are displayed in FIG. 7. FIGS. 8 through 10 displays original tomographic images (left) and images reconstructed from the digital projection radiographs of the cone model (right) in steps of 10% of the thickness from 0% to 100%. FIG. 8 shows the bottom 4 slices 0%, 10%, 20%, and 30%. FIG. 9 shows slices 40%, 50%, 60%, and 70%. FIG. 10 shows slices 80%, 90%, and 100%. Notice that there is only a faint hint of the center 50% slice cross which spilled over into the 40% and 60% reconstruction slices. Notice also the preservation of both the high resolution from the center cross and the lower spatial frequencies from the wall of the cone.

Alternate Embodiments

Figure 11:
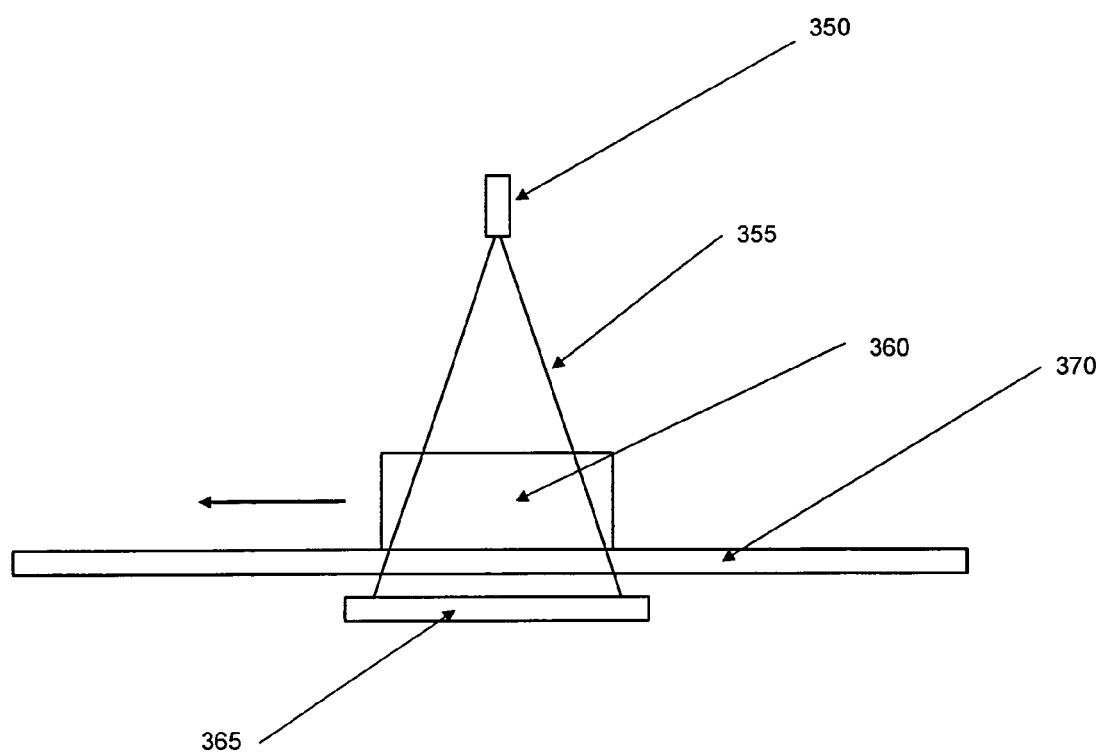
FIGS. 11 and 12 show the side view and front view of a luggage screening system that incorporates the invention.
Figure 12:
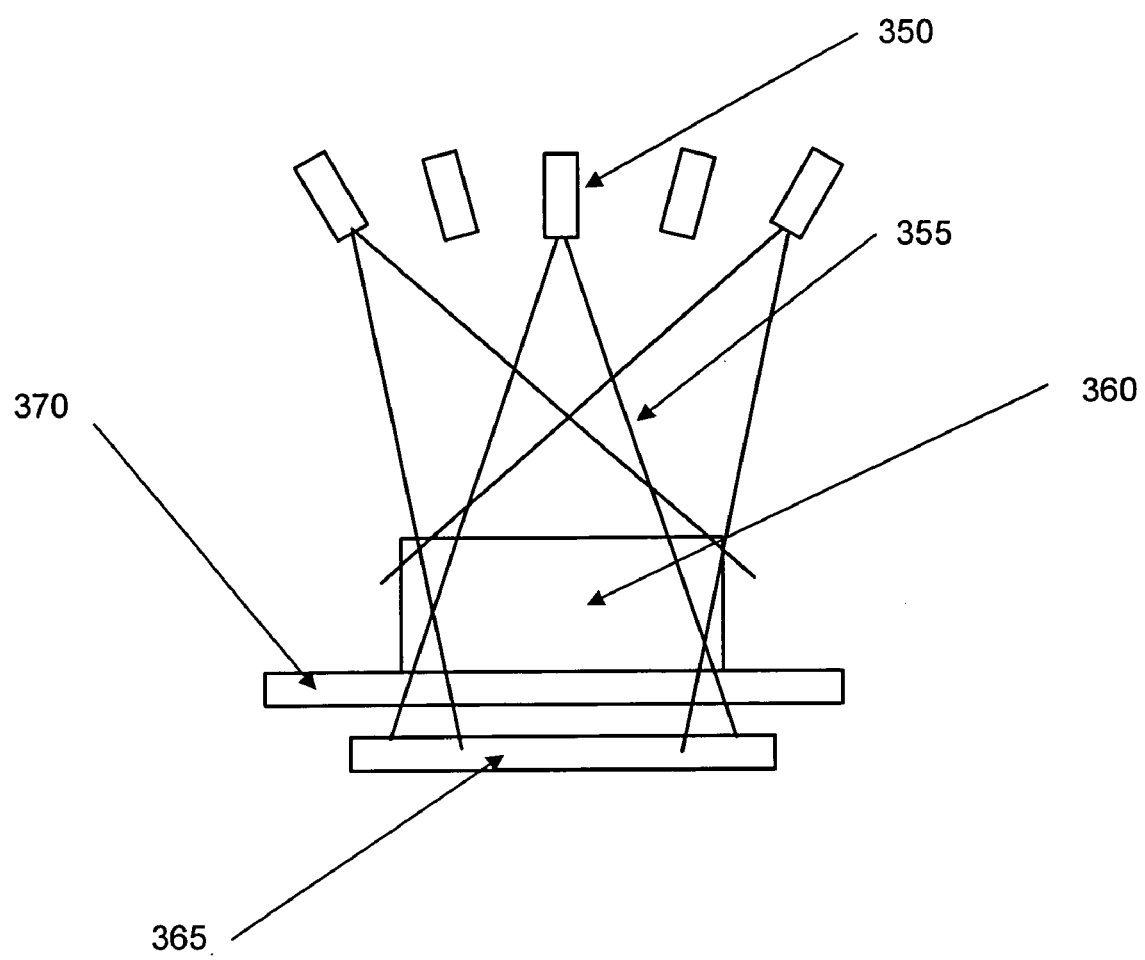

An alternate embodiment of the invention involves the use of multiple x-ray sources in order to provide faster imaging times, and therefore higher throughput. FIG. 11 displays the side views and FIG. 12 the front views of a DXT system that incorporates a line of five x-ray sources 350 in a line that sequentially expose digital x-ray sensor 365 and provide five separate projection radiographs. Conveyor belt 370 re-positions object 360 in a direction perpendicular to the line of x-ray sources 350 to a plurality of positions (8 positions preferred) where x-ray sources 350 provide five digital projection radiographs at each position of object 360 in order to provide a total of 40 projection radiographs; this data is used to reconstruct tomographic images of object 360. This system is useful for luggage inspection. It uses the same basic algorithm as described above.

While there have been shown what are presently considered to be preferred embodiments of the present invention, it will be apparent to those skilled in the art that various changes and modifications can be made herein without departing from the scope and spirit of the invention. For example, prior art techniques can be incorporated for fast readout of data to enable good images of moving parts such as the heart and lungs of people. The invention can be applied to a variety of uses in addition to medical imaging and luggage screening. The invention can be made portable for use by emergency teams and battlefield conditions. Known techniques can be incorporated for automatic recognition of items such as weapons and explosives based on shape and attenuation information. Many modifications could be made to the specific algorithm which has been described in detail without departing from the basic concepts of the present invention. For example other least square techniques other than the one specifically described can be used with generalized functions to turn x-ray data into images.

Thus, the scope of the invention is to be determined by the appended claims and their legal equivalents.

We claim:

1. A digital x-ray tomosynthesis system comprising:
   A) at least one x-ray source,
   B) a two-dimensional digital x-ray image sensor,
   C) an x-ray data collection-positioning mechanism for positioning, relative to each other, said at least one x-ray source, said image sensor and an object for collecting with said image sensor x-ray attenuation data representing attenuation of a large number of rays of x-radiation from said at least one source through said object to said image sensor, and
   D) a computer processor programmed with an algorithm for producing tomographic or three-dimensional images of said object or portions of said object using a least squares technique utilizing generalized non-specific functions;

wherein in said algorithm a three-dimensional object being imaged is represented by a scalar function $d(x_{tomo}, y_{tomo}, h)$ in the dimension of Hounsfield units with one Hounsfield unit equal to a 0.1 % difference in the density of water and the range of Hounsfield units is from −1000 (air) to 1000 (bone) with 0 Hounsfields as the density of water, wherein the attenuation of x-rays directed along a line (trajectory s) is given by $$A_i(s) = A_i\left[\int_0^s d(x_{tomo}, y_{tomo}, h) ds'\right]$$

where $(x_{tomo}, y_{tomo})$ are the coordinates where trajectories cross the tomographic plane at $z=h$.

2. The system as in claim 1 wherein the attenuation of x-rays are expressed in logarithmic units.

3. The system as in claim 2 wherein logarithms of pixelated digital x-ray images acquired by the digital x-ray image sensor are represented by $$m_i(x,y) = m0_i(x,y) + n_i(x,y)$$

where $$m0_i(x,y) = w(x,y) A_i(s) psf(x,y)$$

are noise-free measurements for each N source positions $(X_i, Y_i)$; $i=1,N$, $n_i(x,y)$ is noise, $w_i(x,y)$ is the white field image acquired during calibration, and $psf(x,y)$ is a point spread function.

4. The system as in claim 3 wherein $m0_i(x,y)$ is also represented by:

$$m0_i(x,y) = w(x,y) A$$

$$m0_i(x,y) = w(x,y)$$

$$A\left[\sec\theta_i(x,y) \int_0^{SID} d\left[x\left(1-\frac{h}{SID}\right)+\frac{hX_i}{SID}, y\left(1-\frac{h}{SID}\right)+\frac{hY_i}{SID}, h\right] dh\right] \otimes psf(x,y).$$

5. The system as in claim 4 wherein an equation for $m0_i(x,y)$ is inverted to express a tomographic slice image data $d(x,y,h)$ in terms of the acquired noise free data $m0(x,y)$ by minimizing the following generalized chi-squared function:

$$\chi^2 = \sum_i \int\int (m_i(x_0,y_0) - m0_i(x_0,y_0))[(n(x_0,y_0)n(x_1,y_1))_{avg}]^{-1}(m_i(x_1,y_1) - m0(x_1,y_1)) dx_0 dy_0 dx_1 dy_1 + \varepsilon \int\int d(x,y,h)^2 dx dy dh$$

versus a function $d(x_{tomo}, y_{tomo}, h)$,
where e is a regularization parameter chosen so that the first term averages 1 per measurement and m0 is implicitly a function of $d(x_{tomo}, y_{tomo}, h)$.

6. The system as in claim 5 wherein the equation set forth in claim 4 is simplified to produce an equation:

$$m0(x,y) = w_i(x,y) A\left[\sec\theta_i(x,y) \int_0^\infty D\left(x+\frac{X_i z}{SID}, y+\frac{Y_i z}{SID}, z\right) dz\right] \otimes psf(x,y)$$

and equation set forth in claim 2 is expressed as:

$$\chi^2 = \sum_i \int\int (m_i(x_0,y_0) - m0_i(x_0,y_0))[(n(x_0,y_0)n(x_1,y_1))_{avg}]^{-1}(m_i(x_1,y_1) - m0(x_1,y_1)) dx_0 dy_0 dx_1 dy_1 + \varepsilon \int\int D(x,y,z)^2 dx dy dh.$$

7. The system as in claim 6 wherein a noise correlation is a noise spectrum function (NPS) using the following equation:

$$(n_i(x_0,y_0)n_i(x_1,y_1))_{avg} = \int NPS(x_0-x, y_0-y, x_1-x, y_1-y, x, y) dx d$$

NPS is approximated by:

$$\int NPS(x_0-x, y_0-y, x_1-x, y_1-y, x, y) dx dy = nps(x_0-x_1, y_0-y_1) \sqrt{noise_i(x_0,y_0)} \sqrt{noise_i(x_1,y_1)}$$

where NPS is the noise power spectrum correlation function normalized to 1 at 0 lp/mm.

8. The system as in claim 7 an "integrated Hounsfield" measurement M and its noise free version M0 are is defined according to the equations set forth below:

$$M0_i(x,y) = \int D(x+\alpha z, y+\beta z, z) dz =$$
$$\frac{1}{\sec\theta_i(x,y)} A^{-1}\left[\left(\frac{m0_i(x,y)}{w_i(x,y)}\right) \otimes (psf^{-1}(x,y)) M_i(x,y) = \right.$$
$$\left. \frac{1}{\sec\theta_i(x,y)} A\left[\left(\frac{m_i(x,y)}{w_i(x,y)}\right) \otimes [psf^{-1}(x,y)]\right]\right.$$

where $Mo_i$ is a transform of raw measurements m0.

9. The system as in claim 8 wherein a first order Taylor expansion is used to bring a slowly varying white field term $w_i(x,y)$ outside of the convolution, where the difference of M and M0, i.e.

$$M_i(x, y) - M0_i(x, y) = \frac{(m_i(x, y) - m0_i(x, y)) \otimes (psf^{-1}(x, y))}{\sec\theta_i(x, y)w_i(x, y)A'(M_i(x, y)\sec\theta_i(x, y))}$$

is a transformed noise term and
where $$A'(v) = \frac{d}{dv}A(v).$$

10. The system as in claim 9 wherein $w_i(x,y)A'(M_i(x,y)\sec\theta_i(x,y))$ is the derivative of a signal versus thickness defining "dsignal" which can be calculated or measured and utilized to calculate:

$$m_i(x,y) - m0_i(x,y) = [(M0_i(x,y) - M_i(x,y))dsignal_i(x,y)\sec\theta_i(x,y)]psf(x,y)$$

so that the optimization function set for the in claim 2 is expressed as:

$$\chi^2 = \Sigma\left[\left((M_i - M0_i)\frac{dsignal_i \sec\theta_i}{\sqrt{noise_i}}\right) \otimes psf \otimes (nps^{-1}) \otimes mtf \otimes \left[(M_i - M0_i)\frac{dsignal_i \sec\theta_i}{\sqrt{noise_i}}\right]\right]_{x=0,y=0} + \varepsilon \int\int D(x, y, z)^2 dx\,dy\,dz.$$

11. The system as in claim 10 wherein the convolution in the middle of the last equation of claim 10 defines a detector quantum efficiency $$dqe = psf(nps^{-1})psf$$

that defines a ratio $$\frac{noise}{dsignal^2} = \Delta t2$$

which represents a "thickness noise" squared and $\Delta t2$ is treated as a function only of thickness and can be calculated or measured.

12. The system as in claim 11 wherein a noise function $$\sigma_i(x, y) = \frac{\sqrt{noise_i(x, y)}}{dsignal_i(x, y)}\sec\theta_i(x, y)^{-1} = \sec\theta_i(x, y)^{-1}\sqrt{\Delta t2(M_i(x, y)\sec\theta_i(x, y))}$$

and the last equation set forth in claim 10 is expressed as $$\chi^2 = \sum_i \left[\left(\frac{M_i - \int D(x + \alpha_i z, y + \beta_i z, z)}{\sigma_i(x, y)}\right) \otimes dqe \otimes \left(\frac{M_i - \int D(x + \alpha_i z, y + \beta_i z, z)}{\sigma_i(x, y)}\right)\right]_{x=0, y=0} +$$

-continued $$\varepsilon \int\int D(x, y, z)^2 dx\,dy\,dz$$

which is solved by calculating the derivative of $\chi^2$ versus $D(x_0, y_0, z_0)$ and calculating where this derivative equals 0 to produce:

$$0 = \sum_i \left[\left(\frac{\int D(x + \alpha_i z, y + \beta_i z, z)dz}{\sigma_i(x, y)}\right) \otimes dqe \left.\frac{1}{\sigma_i(x, y)}\right]_{x=x_o-\alpha_i z, y=y_o-\beta_i z} + \varepsilon D(x_o, y_o, z).$$

13. The system as in claim 12 where D is defined from a generator that is discrete, i.e.:

$$D(x, y, z) = \sum_j G(x - \alpha_j z, y - \beta_j z, z)$$

so that the equation set forth in claim 11 becomes:

$$0 = \sum_i \left[\left(\frac{\int \sum_j G(x - \alpha_j z + \alpha_i z, y - \beta_j z + \beta_i z)dz - M_i}{\sigma_i(x, y)}\right) \otimes dge \left.\frac{1}{\sigma_i(x, y)}\right]_{x=x_o-\alpha_i z, y=y_o-\beta_i z} + \varepsilon \sum_i G(x_o - \alpha_i z_o, y_o - \beta_i z_o).$$

14. The system as in claim 13 wherein the i-summation are identically assumed to be equal to zero, so that:

$$0 = \left(\left(\frac{\int \sum_j G(x - \alpha_j z + \alpha_i z, y - \beta_j z + \beta_i z)dz - M_i}{\sigma_i(x, y)}\right) \otimes dge \frac{1}{\sigma_i(x,)} + \varepsilon G_i(x, y).$$

15. The system as in claim 14 wherein the equation in claim 14 is simplified by defining a function C as $$C_{ij}(x, y) = \int_0^{z_{max}} \delta[x + (\alpha_i - \alpha_j)z, y + (\beta_i - \beta_j)z]dz$$

wherein $z_{max}$ in claim 14 equation is determined by the height of an object that is imaged, and the integral excludes absorption below the detector or above $z_{max}$ in the solution so that the last equation of claim 14 is expressed as;

$$dge \otimes \left(\frac{M_i}{\sigma_i}\right) = dge \otimes \left(\frac{C_{ij} \otimes G_j}{\sigma_i}\right) + \varepsilon \sigma_i G_j \text{ (sum over j)}$$

which is solved for G, then D is solved from G and d is solved from D.

16. The system as in claim 15 wherein s in the equation set forth in claim 15 is assumed to be constant, and the equation is inverted using Fourier transforms wherein the convolutions become products $$\Im(dqe)\Im(M_i) = \Im(dqe)\Im(C_{ij})\Im(G_j) + \varepsilon\sigma_i^2 \Im(G_i)$$

where $\Im$ denotes a Fourier transform so that the equation is then expressed as $$\Im(G_1) = (\Im(dqe)\Im(C_{ij}) + \varepsilon\sigma_i^2 \delta_{ij})^{-1} \Im(dqe)\Im(M_i)$$

and the inverses are performed individually over each spatial frequency.

17. The system as in claim 16 wherein inverse matrices are computed once and stored as a look-up table for improved computational speed and stored data is required for each noise level and each value of $z_{max}$.

18. The system as in claim 15 wherein a non-constant s is assumed and multiple iterations are utilized with a constant $\sigma_{trial}$, solving equation the last equation in claim 12 using a Fourier transform method, calculating an error term, then iterating by reconstructing for the error term but using successively different values for the trial $\sigma$ value $\sigma_{trial}$, wherein an the error term is calculated as follows $$\text{error} = dge \otimes \left(\frac{M_i}{\sigma_i}\right) - dge \otimes \left(\frac{C_{ij} \otimes G_j}{\sigma_i}\right) + \varepsilon\sigma_i G_j$$

the error term is inverted using a constant $\sigma$ $$dqe(C_{ij}\Delta G_i) + \varepsilon\sigma_{trial}^2 \Delta G_i = \text{error},$$

then a reconstructed generator coefficients are updated $$G_i \rightarrow G_i + \Delta G_i$$

then the process is repeated with a different value of $\sigma_{trial}$ so that eventually, the "error" becomes sufficiently small that solution is obtained.

19. The system as in claim 18 wherein boundary conditions are handled by reflection conditions with tapering and a minimization function is:

$$\chi^2 = \sum_i \left[\left(\frac{C_{ij} \otimes G_j}{\sigma_i} - \frac{M_i}{\sigma_i}\right) \otimes dge \otimes \left(\frac{C_{ik} \otimes G_k}{\sigma_i} - \frac{M_i}{\sigma_i}\right)\right]_{x=0,y=0} + \varepsilon(G_k \otimes C_{kj} \otimes G_j)|_{x=0,y=0}$$

so the first term equal (# of tube positions)×(# of pixels) when $\varepsilon$ is set correctly.

* * * * *